US010004798B2

(12) United States Patent
Bottje et al.

(10) Patent No.: US 10,004,798 B2
(45) **Date of Patent: *Jun. 26, 2018**

(54) COMPOSITIONS AND METHODS OF ENHANCING IMMUNE RESPONSES

(71) Applicants: THE BOARD OF TRUSTEES OF THE UNIVERSITY OF ARKANSAS, Little Rock, AR (US); THE TEXAS A&M UNIVERSITY SYSTEM, College Station, TX (US)

(72) Inventors: Walter Bottje, Fayetteville, AR (US); Billy Hargis, Fayetteville, AR (US); Luc Berghman, College Station, TX (US); Young Min Kwon, West Fork, AR (US); Kimberly Cole, Raymond, OH (US); Mandy Cox, Fayetteville, AR (US); Sherryll Layton, Rogers, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/971,704

(22) Filed: Dec. 16, 2015

(65) Prior Publication Data
US 2016/0114025 A1 Apr. 28, 2016

Related U.S. Application Data

(63) Continuation of application No. 14/100,957, filed on Dec. 9, 2013, now Pat. No. 9,226,957, which is a continuation of application No. 12/441,851, filed as application No. PCT/US2007/078785 on Sep. 18, 2007, now Pat. No. 8,604,178.

(60) Provisional application No. 60/825,983, filed on Sep. 18, 2006.

(51) Int. Cl.

| | |
|---|---|
| *A61K 39/112* | (2006.01) |
| *A61K 49/00* | (2006.01) |
| *A61K 39/38* | (2006.01) |
| *A61K 39/145* | (2006.01) |
| *C12N 15/10* | (2006.01) |
| *A61K 39/12* | (2006.01) |
| *A61K 35/74* | (2015.01) |
| *A61K 39/00* | (2006.01) |
| *C07H 21/04* | (2006.01) |
| *A61K 35/00* | (2006.01) |

(52) U.S. Cl.

CPC ............ *A61K 39/145* (2013.01); *A61K 35/74* (2013.01); *A61K 39/0275* (2013.01); *A61K 39/12* (2013.01); *C12N 15/102* (2013.01); *A61K 39/00* (2013.01); *A61K 2035/11* (2013.01); *A61K 2039/522* (2013.01); *A61K 2039/523* (2013.01); *A61K 2039/552* (2013.01); *A61K 2039/55516* (2013.01); *A61K 2039/6006* (2013.01); *A61K 2039/6031* (2013.01); *C07H 21/04* (2013.01); *C12N 2760/16134* (2013.01)

(58) Field of Classification Search
CPC ..... A61K 39/00; A61K 39/02; A61K 39/0275
USPC ..... 424/9.1, 9.2, 184.1, 185.1, 234.1, 258.1; 536/23.1, 23.7
See application file for complete search history.

(56) References Cited

U.S. PATENT DOCUMENTS

| | | | |
|---|---|---|---|
| 5,683,700 A | 11/1997 | Charles et al. | |
| 5,747,309 A | 5/1998 | Allan et al. | |
| 5,962,406 A | 10/1999 | Armitage et al. | |
| 5,981,724 A | 11/1999 | Armitage et al. | |
| 6,087,329 A | 7/2000 | Armitage et al. | |
| 6,190,669 B1 | 2/2001 | Noriega et al. | |
| 6,264,951 B1 | 7/2001 | Armitage et al. | |
| 6,290,972 B1 | 9/2001 | Armitage et al. | |
| 6,306,387 B1 | 10/2001 | Galan | |
| 6,410,711 B1 | 6/2002 | Armitage et al. | |
| 6,902,906 B1 | 6/2005 | Chatfield | |
| 6,923,957 B2 | 8/2005 | Lowery et al. | |
| 6,923,958 B2 | 8/2005 | Xiang et al. | |
| 6,936,425 B1 | 8/2005 | Hensel et al. | |
| 6,969,609 B1 | 11/2005 | Schlom et al. | |
| 7,087,573 B1 | 8/2006 | Lazarus et al. | |
| 7,332,298 B2 | 2/2008 | Kornbluth | |
| 7,371,392 B2 | 5/2008 | Tripp et al. | |
| 7,405,270 B2 | 7/2008 | Armitage et al. | |
| 7,495,090 B2 | 2/2009 | Prussak et al. | |
| 7,842,501 B2 | 11/2010 | Cai et al. | |
| 7,928,213 B2 | 4/2011 | Prussak et al. | |
| 8,604,178 B2 * | 12/2013 | Bottje | A61K 39/0275 424/234.1 |

(Continued)

FOREIGN PATENT DOCUMENTS

| | | |
|---|---|---|
| WO | WO 1993/008207 | 4/1993 |
| WO | WO 1995/014487 | 6/1995 |

(Continued)

OTHER PUBLICATIONS

Agterberg, M. et al., "Outer membrane protein PhoE as a carrier for the exposure of foreign antigenic determinants at the bacterial cell surface," Antonie Van Leeuwenhoek (1991) 59(4):249-262.

(Continued)

*Primary Examiner* — Rodney P Swartz
(74) *Attorney, Agent, or Firm* — Andrus Intellectual Property Law, LLP

(57) ABSTRACT

Provided herein are *Salmonella enteritidis* 13A strains and compositions comprising these strains. Also provided are methods of enhancing an immune response against Influenza A and methods of reducing morbidity associated with an Influenza A infection. Methods of enhancing an immune response to a vaccine vector by expressing a polypeptide of CD154 capable of binding CD40 are also disclosed. Methods of developing a bacterial vaccine vector are disclosed. Methods of generating scarless site-specific mutations in a bacterium are also disclosed.

17 Claims, 8 Drawing Sheets

(56) References Cited

U.S. PATENT DOCUMENTS

| | | | | |
|---|---|---|---|---|
| 8,956,849 | B2* | 2/2015 | Bottje | A61K 39/002 435/235.1 |
| 9,125,854 | B2* | 9/2015 | Bottje | A61K 39/0275 |
| 2001/0021386 | A1 | 9/2001 | Nuijten et al. | |
| 2003/0045492 | A1 | 3/2003 | Tang et al. | |
| 2004/0047873 | A1 | 3/2004 | Al-Shamkhani et al. | |
| 2004/0203039 | A1 | 10/2004 | Hensel et al. | |
| 2005/0181994 | A1 | 8/2005 | Chamberlain et al. | |
| 2005/0226888 | A1 | 10/2005 | Deisseroth et al. | |
| 2006/0014248 | A1 | 1/2006 | Marshall et al. | |
| 2006/0078994 | A1 | 4/2006 | Healey et al. | |
| 2006/0233829 | A1 | 10/2006 | Curtiss | |
| 2006/0286074 | A1 | 12/2006 | Tang et al. | |
| 2007/0025982 | A1 | 2/2007 | Ledbetter et al. | |
| 2007/0082400 | A1 | 4/2007 | Healey et al. | |
| 2007/0128223 | A1 | 6/2007 | Tang et al. | |
| 2007/0237779 | A1 | 10/2007 | Ledbetter et al. | |
| 2010/0047231 | A1 | 2/2010 | Zabaleta Azpiroz et al. | |

FOREIGN PATENT DOCUMENTS

| | | |
|---|---|---|
| WO | WO 1996/026735 | 9/1996 |
| WO | WO 1996/040918 | 12/1996 |
| WO | WO 1999/027948 | 6/1999 |
| WO | WO 1999/032138 | 7/1999 |
| WO | WO 2000/063395 | 10/2000 |
| WO | WO 2000/063405 | 10/2000 |
| WO | WO 2001/042298 | 6/2001 |
| WO | WO 2001/056602 | 8/2001 |
| WO | WO 2002/030461 | 4/2002 |
| WO | WO 2002/036769 | 5/2002 |
| WO | WO 2002/092773 | 11/2002 |
| WO | WO 2003/004683 | 1/2003 |
| WO | WO 2003/004684 | 1/2003 |
| WO | WO 2003/099340 | 12/2003 |
| WO | WO 2004/009615 | 1/2004 |
| WO | WO 2004/046345 | 6/2004 |
| WO | WO 2005/035570 | 4/2005 |
| WO | WO 2005/058950 | 6/2005 |
| WO | WO 2005/113598 | 12/2005 |
| WO | WO 2006/012373 | 2/2006 |
| WO | WO 2006/042177 | 4/2006 |
| WO | WO 2006/105972 | 10/2006 |
| WO | WO 2007/042583 | 4/2007 |
| WO | WO 2007/054658 | 5/2007 |
| WO | WO 2007/056266 | 5/2007 |
| WO | WO 2007/103048 | 9/2007 |
| WO | WO 2007/117682 | 10/2007 |
| WO | WO 2008/109825 | 9/2008 |
| WO | 2013/071298 | 5/2013 |

OTHER PUBLICATIONS

Barr, T.A. et al., "A potent adjuvant effect of CD40 antibody attached to antigen," Immunology (2003) 109:87-92.
Black, R.A. et al., "Antibody response to the M2 protein of influenza A virus expressed in insect cells," J. Gen. Virol. (1993) 74(Pt.1):143-146.
Blomfield, I.C. et al., "Allelic exchange in Escherichia coli using the Bacillus subtilis sacB gene and a temperature-sensitive pSC101 replicon," Mol Microbiol (1991) 5(6):1447-1457.
Capua, I. et al., "The challenge of avian influenza to the veterinary community," Avian Pathol. (2006) 35:189-205.
Capua, I. et al., "Vaccination for avian influenza in Asia," Vaccine (2004) 22:4137-4138.
Capua, I. et al, "Control of avian influenza in poultry," Emerg. Infect. Dis. (2006) 12:1319-1324.
Charbit, A. et al., "Probing the topology of a bacterial membrane protein by genetic insertion of a foreign epitope; expression at the cell surface," EMBO J (1986) 5(11):3029-3037.
Charbit, A. et al., "Versatility of a vector for expressing foreign polypeptides at the surface of gram-negative bacteria," Gene (1988) 70(1):181-189.

Chatfield et al., "The development of oral vaccines based on live attenuated Salmonella strains," FEMS Immunol. Med. Microbiol. (1993) 7:1-7.
Cole, K. et al., "Evaluation of a novel recombinant Salmonella vaccine vector for avian influenza," Poultry Science (2007) 86(Supp.1):585-586.
Cox, M.M. et al., "Scarless and site-directed mutagenesis in Salmonella enteritidis chromosome," BMC Biotech. (2007) 7(59):10 pages.
De Filette, M. et al, "The universal influenza vaccine M2e-HBc administered intranasally in combination with the adjuvant CTA1-DD provides complete protection," Vaccine (2006) 24:544-551.
De Filette, M. et al., "Universal influenza A vaccine: Optimization of M2-based constructs," Virology (2005) 337:149-161.
De Filette, M. et al., "Improved design and intranasal delivery of an M2e-based human influenza A vaccine," Vaccine (2006) 24:6597-6601.
Ellis, R.W., "New technologies for making vaccines," (1988) Vaccines, Chapter 29:568-574.
Ernst, W.A. et al., "Protection against H1, H5, H6 and H9 influenza A infection with liposomal matrix 2 epitope vaccines," Vaccine (2006) 24:5158-5168.
Fan, J. et al., "Preclinical study of influenza virus A M2 peptide conjugate vaccines in mice, ferrets and rhesus monkeys," Vaccine (2004) 22:2993-3003.
Farnell, M.B. et al., "Upregulation of oxidative burst and degranulation in chicken heterophils stimulated with probiotic bacteria," Poult. Sci. (2006) 85:1900-1906.
Fecteau, J.F. et al., "CD40 Stimulation of Human Peripheral B Lymphocytes: Distinct Response from Naïve and Memory Cells," J Immunol (2003) 171:4621-4629.
Fernandez-Cabezudo et al., "Evidence for the requirement for CD40-CD154 interactions in resistance to infections with attenuated Salmonella," J. Endotoxin Res. (2005) 11:395-399.
Fiers, W. et al., "A universal human influenza A vaccine," Virus Research (2004) 103:173-176.
Frace, A.M. et al., "Modified M2 proteins produce heterotypic immunity against influenza A virus," Vaccine (1999) 17:2237-2244.
Gao, w. et al., "Protection of mice and poultry from lethal H5N1 avian influenza virus through adenovirus-based immunization," J. Virol. (2006) 80:1959-1964.
Gares, S.L. et al., "Immunotargeting with CD154 (CD40 ligand) enhances DNA vaccine responses in ducks," Clin. Vaccine Immun. (2006) 13:958-965.
Gast, R.K. et al., "The relationship between the magnitude of the specific antibody response to experimental Salmonella enteritidis infection in laying hens and their production of contaminated eggs," Avian Diseases (2001) 45:425-431.
Grewal, I.S. et al., "CD40 and CD154 in cell-mediated immunity," Annu. Rev. Immunology. (1998) 16:111-35.
Harcourt, J.L. et al., "CD40 ligand (CD154) improves the durability of respiratory syncytial virus DNA vaccination in BALB/c mice," Vaccine (2003) 21(21-22):2964-2979.
Hayes, L.J. et al., "Chlamydia trachomatis major outer membrane protein epitopes expressed as fusions with LamB in an attenuated aro A strain of Salmonella typhimurium; their application as potential immunogens," Journal of General Microbiology (1991) 137:1557-1564.
Heinen, P.P. et al., "Vaccination of pigs with a DNA construct expressing an influenza virus M2-nucleoprotein fusion protein exacerbates disease after challenge with influenza A virus," Journal of General Virology (2002) 83(8):1851-1859.
Herrero, M. et al., "Transposon vectors containing non-antibiotic resistance selection markers for cloning and stable chromosomal insertion of foreign genes in gram-negative bacteria," J Bacteriol (1990) 172(11):6557-6567.
Holmgren, J. et al., "Mucosal immunity: implications for vaccine development," Immunobiol. (1992) 184:157-179.
Husseiny, M.L. et al., "Rapid method for the construction of Salmonella enterica serovar typhimurium vaccine carrier strains," Infec. Immun. (2005) 73(3):1598-1605.
Kaiser, J., "A one-size-fits-all flu vaccine?," Science (2006) 312:380-382.

(56) References Cited

OTHER PUBLICATIONS

Kim, E.-H. et al., "Prokaryote-expressed M2e protein improves H9N2 influenza vaccine efficacy and protection against lethal influenza in virus in mice," Virol. J.. (2013) 10(104):1-11.
Koch, F. et al., "High level IL-12 production by murine dendritic cells: upregulation via MHC class II and CD40 molecules and downregulation by IL-4 and IL-10," J. Exp. Med. (1996) 184:741-746.
Kodihalli, S. et al., "Cross-protection among lethal H5N2 influenza viruses induced by DNA vaccine to the hemagglutinin," J. Virol. (1997) 71:3391-3396.
Kotton, C.N. et al., "Enteric pathogens as vaccine vectors for foreign antigen delivery," Infect. Immun. (2004) 72:5535-5547.
Kwon, Y.M. et al., "*Salmonella*-based vaccines for infectious diseases," Expert Review of Vaccines (2007) 6(2):147-152.
Lapalombella, R. et al., "A Novel Raji-Burkitt's Lymphoma Model for Preclinical and Mechanistic Evaluation of CD52-Targeted Immunotherapeutic Agents," Clin. Cancer Res. (2008) 14:569-578.
Lavelle, E.C. et al., "Delivery systems and adjuvants for oral vaccines," Expert Opin. Drug Deliv. (2006) 3(6):747-762.
Layton, S.L., et al., "Vaccination of chickens with recombinant *Salmonella* expressing M2e and CD154 epitopes increases protection and decreases viral shedding after low pathogenic avian influenza challenge," Poultry Science (2009) 88(11):2244-2252.
Lee, J. et al., "Mucosal immunization with surface-displayed severe acute respiratory syndrome coronavirus spike protein on Lactobacillus casei induces neutralizing antibodies in mice," J. Virol. (2006) 80:4079-4087.
Lee, J.S. et al., "Surface-displayed viral antigens on *Salmonella* carrier vaccine," Nat. Biotechnol. (2000) 18:645-648.
Li, W., "Synergistic antibody induction by antigen-CD40 ligand fusion protein as improved immunogen," Immunology (2005) 115(2):215-222.
Liu, W. et al., "Monoclonal antibodies recognizing EVETPIRN epitope of influenza A virus M2 protein could protect mice from lethal influenza A virus challenge," Immunol. Lett. (2004) 93:131-136.
Liu, W. et al., "Sequence comparison between the extracellular domain of M2 protein human and avian influenza A virus provides new information for bivalent influenza vaccine design," Microbes and Infection (2005) 7:171-177.
Liu, M. et al., "Display of avian influenza virus nucleoprotein on *Bacillus thuringiensis* cell surface using CTC as a fusion partner," Applied Genetics and Molecular Biotechnology (2008) 78:669-676.
Lowe, D.C. et al., "Characterization of candidate live oral *Salmonella typhi* vaccine strains harboring defined mutations in aroA, aroC, and htrA," Infection and Immunity Feb. 1999:700-707.
Manoj, S. et al., "Targeting with Bovine CD154 enhances humoral immune responses induced by a DNA vaccine in sheep," (2003) Journal of Immunology 170:989-996.
Mendoza, R.B. et al., "Cutting edge: Immunostimulatory effects of a plasmid expressing CD40 ligand (CD154) on gene immunization," Journal of Immunology (1997) 159(12):5777-5781.
Miga, A. et al., "The role of CD40-CD154 interactions in the regulation of cell mediated immunity," Immunol Invest. (2000) 29:111-114.
Mogensen, T.H., "Pathogen recognition and inflammatory signaling in innate immune defenses," Clin. Microbiol. Rev. (2009) 22(2):240-273.
Mohamadzadeh, M. et al., "Targeting mucosal dendritic cells with microbial antigens from probiotic lactic acid bacteria," Expert Rev. Vaccines (2008) 7(2):163-174.
Monteilhet, C. et al., "Purification and characterization of the in vitro activity of I-Sce I, a novel and highly specific endonuclease encoded by a group I intron," Nucleic Acids Res. (1990) 18(6):1407-1413.
Moyle, P.M. et al., "Mucosal immunisation: adjuvants and delivery systems," Curr. Drug Deliv. (2004) 1(4):385-396.
Mozdzanowska, K. et al., "Induction of influenza type A virus-specific resistance by immunization of mice with a synthetic multiple antigenic peptide vaccine that contains ectodomains of matrix protein 2," Vaccine (2003) 21:2616-2626.
Nakajima, A. et al., "Antitumor effect of CD40 ligand: Elicitation of local and systemic antitumor responses by IL-12 and B7," (1998) Journal of Immunology 161:1901-1907.
Neirynck, S. et al., "A universal influenza A vaccine based on the extracellular domain of the M2 protein," Nat. Med. (1999) 5:1157-1163.
Ninomiya, A. et al., "Intranasal administration of a synthetic peptide vaccine encapsulated in liposome together with an anti-CD40 antibody induces protective immunity against influenza A virus in mice," Vaccine (2002) 20:3123-3129.
O'Callaghan, D. et al., "Immunogenicity of foreign peptide epitopes expressed in bacterial envelope proteins," Research in Microbiology (1990) 141:963-969.
Ochoa-Reparaz, J. et al., "Humoral immune reponse in hens naturally infected with *Salmonella enteritidis* against outer membrane proteins and other surface structural antigens," (2004) Vet. Res. 35:291-298.
Palese, P. et al., "Influenza vaccines: present and future," J. Clin. Invest. (2002) 110:9-13.
Pasetti, M. et al., "Animal models paving the way for clinical trials of attenuated *Salmonella enterica* servoar Typhi live oral vaccines and live vectors," Vaccine (2003) 21:401-418.
Russmann, H. et al., "Delivery of epitopes by the *Salmonella* type III secretion system for vaccine development," Science (1998) 281(5376):565-568.
Slepushkin, V.A. et al., "Protection of mice against influenza A virus challenge by vaccination with baculovirus-expressed M2 protein," Vaccine (1995) 13:1399-1402.
Su, G.F. et al., "Construction of stable LamB-Shiga toxin B subunit hybrids: analysis of expression in *Salmonella typhimurium* aroA strains and stimulation of B subunit-specific mucosal and serum antibody responses," Infect Immun (1992) 60(8):3345-3359.
Swayne, D.E. et al., "Protection against diverse highly pathogenic H5 avian influenza viruses in chickens immunized with a recombinant fowlpox vaccine containing an H5 avian influenza hemagglutinin gene insert,". Vaccine (2000) 18:1088-1095.
Swayne, D.E., "Vaccines for List A poultry diseases: emphasis on avian influenza," Dev. Biol. (2003) 114:201-212.
Tang, M. et al., "Recombinant adenovirus encoding the HA gene from swine H3N2 influenza virus partially protects mice from challenge with heterologous virus: A/HK/1/68 (H3N2)," Arch. Virol. (2002) 147:2125-2141.
Tischer, B.K. et al., "Two-step red mediated recombination for versatile high-efficiency markerless DNA manipulation in *Escherichia coli*," Biotechniques (2006) 40(2):191-197.
Tompkins, S.M. et al., "Matrix protein 2 vaccination and protection against influenza viruses, including subtype H5N1," Emerging Infectious Diseases (2007) 13(3):426-435.
Tregaskes, C.A. et al., "Conservation of biological properties of the CD40 ligand, CD154 in a non-mammalian vertebrate," Dev. Comp. Immunol. (2005) 29:361-374.
Tumpey, T.M. et al., "Comparative susceptibility of chickens and turkeys to avian influenza A H7N2 virus infection and protective efficacy of a commerical avian influenza H7N2 virus vaccine," Avian Dis. (2004) 48(1):167-176.
Verjans, G.M. et al., "Intracellular processing and presentation of T cell epitopes, expressed by recombinant *Escherichia coli* and *Salmonella typhimurium*, to human T cells," Eur J Immunol (1995) 25(2):405-410.
Vierira-Pinto, M. et al.., "Occurrence of *Salmonella* in the ileum, ileocolic lymph nodes, tonsils, mandibular lymph nodes and carcasses of pigs slaughtered for consumption," J Vet Med B Infection Dis Vet Public Health (2005) 52(10):476-81.
Wang, J. et al., "Immunogenicity of viral B-cell epitopes inserted into two surface loops of the *Escherichia coli* K12 LamB protein and expressed in an attenuated aroA strain of *Salmonella typhimurium*," Vaccine (1999) 17(1):1-12.

(56) References Cited

OTHER PUBLICATIONS

Zebedee, S.L. et al., "Influenza A virus M2 protein: monoclonal antibody restriction of virus growth and detection of M2 in virions," J. Virol. (1988) 62:2762-2772.
Zharikova, D. et al., "Influenza type A virus escape mutants emerge in vivo in the presence of antibodies to the ectodomain of matrix protein 2," J. Virol. (2005) 79:6644-6654.
Zou, P. et al., "The epitope recognized by a monoclonal antibody in influenza A virus M2 protein is immunogenic and confers immune protection," Int. Immunopharmacol. (2005) 5:631-635.
European Patent Office Search Report for Application No. 07842706.9 dated Jan. 5, 2010 (8 pages).
International Search Report and Written Opinion of the International Searching Authority for Application No. PCT/US07/78785 dated Sep. 29, 2008 (11 pages).
International Search Report and Written Opinion for Application No. PCT/US08/81813 dated May 12, 2009 (13 pages).
Written Opinion of the Intellectual Property Office of Singapore for Application No. 2009018599 dated May 13, 2010 (9 pages).
Written Opinion of the Intellectual Property Office of Singapore for Application No. 2009018599 dated Jan. 21, 2011 (7 pages).
Examination Report of the Intellectual Property Office of Singapore for Application No. 2009018599 dated Aug. 4, 2011 (6 pages).
Office Action for Chinese Patent Application No. 200780037288.8 dated Mar. 27, 2012 (8 pages).
European Patent Office Action for Application No. 07842706.9 dated Apr. 11, 2012 (6 pages).
Office Action for Philippine Patent Application No. 1-2009-500491 dated May 30, 2012 (2 pages).
Office Action for U.S. Appl. No. 12/441,851 dated Sep. 5, 2012 (12 pages).
European Patent Office Search Report for Application No. 12165985.8 dated Sep. 20, 2012 (11 pages).
European Patent Office Action for Application No. 07842706.9 dated Sep. 26, 2012 (4 pages).
Office Action for U.S. Appl. No. 12/441,851 dated May 8, 2013 (8 pages).
Office Action for European Patent Application No. 12165985.8 dated Nov. 14, 2014 (5 pages).
European Patent Office Search Report for Application No. 14173324 dated May 6, 2015 (11 pages).
Grangette, C. et al., Protection against tetanus toxin after intragastric adminstration of two recombinant lactic acid bacteria: Impact and strain viability and in vivo persistence, Vaccine (2002) 20:3304-3309.
Katz, J.M. et al., "Adjuvant activity of the heat-labile enterotoxin from enterotoxigenic *Escherichia coli* for oral administration of inactivated influenza virus vaccine," J. Infect. Dis. (1997) 175:352-363.
Rabsch, W. et al., "Competitive exclusion of *Salmonella enteritidis* by *Salmonella gallinarum* in poultry," Emerging Inf. Diseases (2000) 6(5):443-448.
Vega, M.L. et al., "A *Salmonella typhi* OmpC fusion protein expressing the CD154 Trp140-Ser149 amino acid strand binds CD40 and activates a lymphoma B-cell line," Immunol. (2003) 110:206-216.
Xu, Y. et al., "The role of CD40-CD154 interaction in cell immunoregulation," J. Biomed. Sci. (2004) 11:426-438.
Gast, .K., et al., Deposition of Phage Type 4 and 13a *Salmonella enteritidis* strains in the Yolk and Albumen of eggs laid by experimentally infected hens, Avian Diseases, 2000, pp. 706-710, vol. 44:3.
Sinha, K., et al., *Salmonella typhimurium* aroA, htrA, and aroD htrA mutants cause progressive infections in athymic (nu/nu) BALB/c mice, Infection and Immunity, 1997, pp. 1566-1569, vol. 65:4.

\* cited by examiner

Viral Shedding Following Direct Challenge with LPAI H7N2

Legend: Oral NV/C, Oral V/C, Cloacal NV/C, Cloacal V/C n=10 for NV and V

Y-axis: Percentage chicks positive (0–100)
X-axis: Day 2, Day 4

FIG. 6

Morbidity Following Direct Challenge with HPAI H5N1

FIG. 7

Days Post Challenge

% Morbitity

Viral Shedding Following Direct Challenge with HPAI H5N1

FIG. 8

Legend: Oral NV/C, Oral V/C, Cloacal NV/C, Cloacal V/C n=10 for NV and V

COMPOSITIONS AND METHODS OF ENHANCING IMMUNE RESPONSES

CROSS-REFERENCE TO RELATED APPLICATIONS

This application is a continuation of patent application Ser. No. 14/100,957, filed Dec. 9, 2013, now issued as U.S. Pat. No. 9,226,957, on Jan. 5, 2016, which is a continuation of U.S. Pat. No. 8,604,178, issued Dec. 10, 2013, which is a national stage filing under 35 U.S.C. 371 of International Application No. PCT/US2007/078785, filed Sep. 18, 2007, which claims priority to U.S. Provisional Patent Application No. 60/825,983, filed Sep. 18, 2006, all of which are incorporated herein by reference in their entirety.

STATEMENT REGARDING FEDERALLY SPONSORED RESEARCH

This invention was made with United States government support under R21 AI063137 awarded by the National Institutes of Health (NIH). The Government has certain rights in the invention.

INTRODUCTION

Influenza virus infection, particularly avian influenza H5N1, presents a mounting health and economic concern. Evidence clearly indicates that H5N1 is continuing to circulate between susceptible birds and swine in widening regions of the world. Many scientists believe that if left unchecked, the current H5N1 avian influenza will mutate to allow for human to human transmission and cause a worldwide pandemic. With a mortality rate of over 50%, such an outbreak would be devastating. Regardless of the ability of the virus to cause human disease, avian influenza H5N1 is already threatening to have a huge economic impact due to the eradication of poultry flocks in affected areas. Therefore, development of a vaccine to protect humans, poultry, swine and other domesticated animals from H5N1 influenza is needed. An influenza vaccine that is capable of protecting against H5N1 as well as other influenza viruses would be optimal.

SUMMARY

*Salmonella enteritidis* 13A strains having ATCC deposit numbers PTA-7871, PTA-7872 or PTA-7873 are disclosed. Also disclosed is a composition comprising an attenuated *Salmonella* strain and a pharmaceutically acceptable carrier.

In another aspect, methods of enhancing an immune response in a subject by administering a vaccine vector to the subject are provided. A polynucleotide encoding a polypeptide of CD154 capable of binding CD40, the polypeptide having fewer than 50 amino acids and comprising amino acids 140-149 of SEQ ID NO:26 or a homolog thereof. The vaccine vector is administered to the subject in an amount effective to enhance the immune response of the subject to the vaccine.

In a further aspect, methods of enhancing the immune response against Influenza A in a subject by administering to the subject a bacterium comprising a polynucleotide encoding a polypeptide of Influenza A M2e protein in an amount effective to enhance the immune response of the subject to Influenza A are provided.

In yet another aspect, methods of reducing the morbidity associated with Influenza A infection in a subject by administering to the subject a bacterium comprising a polynucleotide encoding a polypeptide of Influenza A M2e protein in an amount effective to reduce the morbidity associated with a subsequent infection with Influenza A are provided.

In still another aspect, methods of generating site-specific mutations in a bacterium are provided. A first polynucleotide comprising a counter-selection marker and an antibiotic resistance marker flanked by polynucleotides homologous to the sequences flanking a mutation site in the chromosome of the bacterium is generated. The first polynucleotide is then introduced into the bacterium and after homologous recombination and antibiotic selection an intermediate is isolated. A second polynucleotide comprising the mutation flanked by polynucleotides homologous to sequences flanking the mutation site is generated. The second polynucleotide is then introduced into the intermediate and the site-specific mutant is isolated by counter-selecting for loss of the counter-selection marker.

In a still further aspect, methods for developing bacterial vaccine vectors are provided. A bacterium capable of colonizing a subject is selected. The bacterium is attenuated and a polynucleotide comprising a sequence encoding a polypeptide of CD154 capable of binding to CD40 is incorporated into the bacterium.

BRIEF DESCRIPTION OF THE DRAWINGS

FIG. 6 is a graph showing viral shedding at days 2 and 4 post-challenge with a low pathogenicity Influenza A after vaccination with SE HM at day-of-hatch, boost at day 21 and challenge infection at day 32 post-hatch.

FIG. 7 is a graph showing the morbidity of chickens after vaccination with SE HM at day-of-hatch, boost at day 21 and challenge infection with a high pathogenicity Influenza A at 32 days post-hatch.

FIG. 8 is a graph showing viral shedding at days 2 and 4 post-challenge with a high pathogenicity Influenza A after vaccination with SE HM at day-of-hatch, boost at day 21 and challenge infection at day 32 post-hatch.

DETAILED DESCRIPTION

Figure 1:
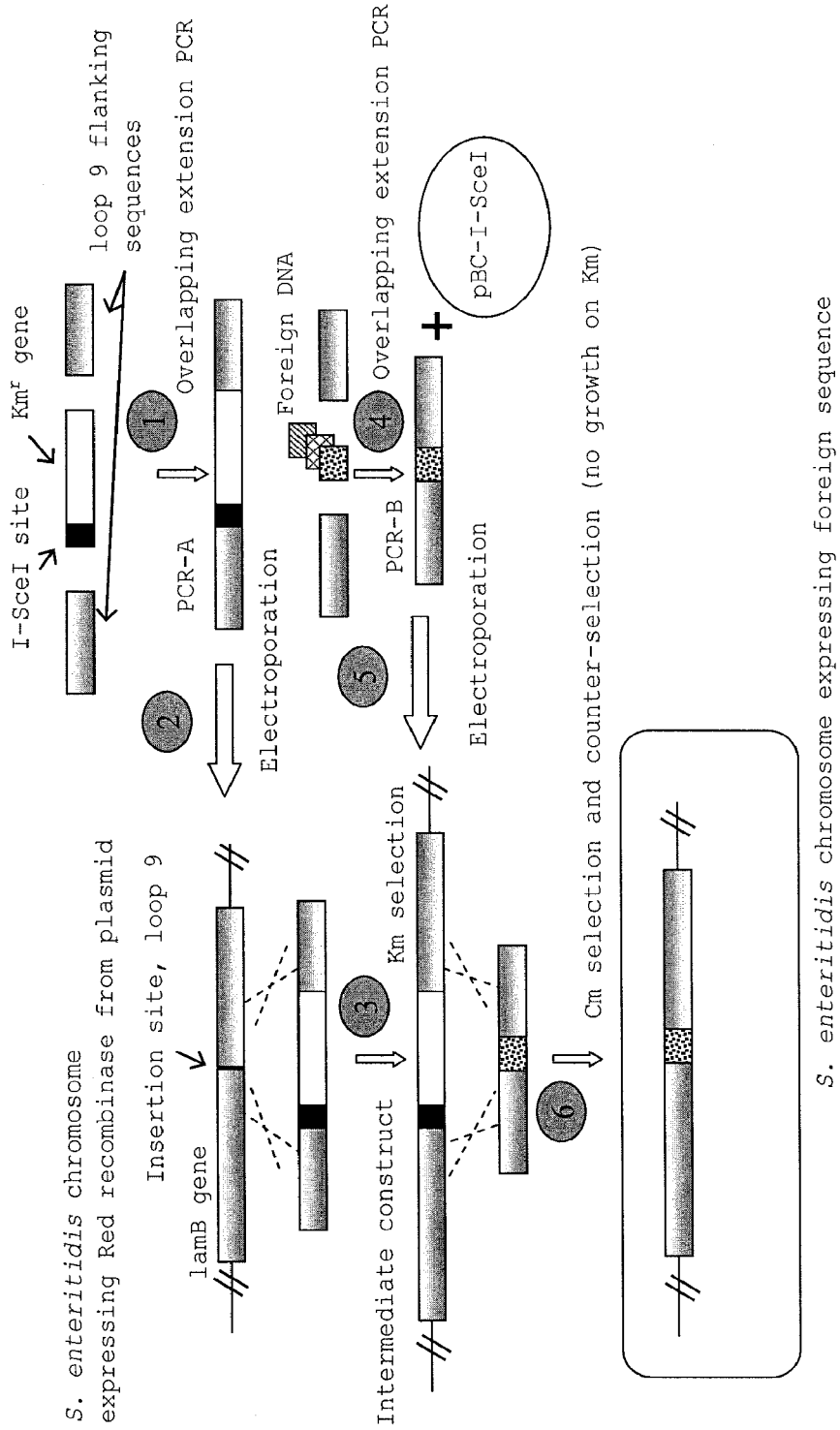
FIG. 1 depicts the scheme for making site-directed mutations in *Salmonella enteritidis*.

Recombinant DNA technologies enable relatively easy manipulation of many bacterial and viral species. Some bacteria and viruses are mildly or non-pathogenic, but are capable of generating a robust immune response. These bacteria and viruses make attractive vaccine vectors for eliciting an immune response to a heterologous or foreign antigen. Bacterial or viral vaccine vectors may mimic the natural infection and produce robust and long lasting immunity. Vaccine vectors are often relatively inexpensive to produce and administer. In addition, such vectors can often carry more than one antigen and may provide protection against multiple infectious agents.

In one aspect, this invention relates to the use of *Salmonella* vectors in vaccination and generation of immune responses against *Salmonella* and other pathogenic agents. *Salmonella* strains make suitable vaccine vectors because of the ability to make bacteria capable of expressing heterologous polypeptides. In addition, bacterial genes may be mutated or attenuated to create bacteria with low to no pathogenesis to the infected or immunized subject, while maintaining immunogenicity.

The ability of the *Salmonella* to survive the gastrointestinal tract of the host and give rise to a mucosal immune response is documented. Oral vaccines using a *Salmonella* vector produce a robust mucosal immune response and are relatively easy to administer to both animals and humans. Many of the current *Salmonella* vaccine strains are not as effective in generating a strong protective immune response as compared to their more virulent counterparts. A *Salmonella* strain that could be used for effective mucosal, e.g., oral, vaccination would provide a vector that could be used to readily vaccinate a subject against one or more pathogenic agents, such as H5N1 influenza.

A *Salmonella enteritidis* strain useful as a vaccine vector, and various recombinant vaccine vectors made using this strain, are described. Specifically, a vaccine vector carrying the M2e epitope of Influenza A virus is provided. In addition, methods of developing vaccine vectors and methods of enhancing an immune response in a subject by administering a vaccine vector comprising a polynucleotide encoding a polypeptide of CD154 or a homolog thereof that is capable of binding to CD40 are disclosed. The vaccine vectors may be used to enhance an immune response against Influenza A or to reduce the morbidity associated with Influenza A infection. Finally, a method of generating site-specific mutations in a bacterium using the Red recombination system in conjunction with overlapping extension PCR to generate mutants containing no extraneous DNA is provided.

A wild-type isolate of *Salmonella, Salmonella enteritidis* 13A (SE13A) (deposited with the American Type Culture Collection (ATCC) on Sep. 13, 2006, deposit number PTA-7871), was selected based upon its unusual ability to cause mucosal colonization and submucosal translocation in chickens, permitting robust presentation of associated antigens or epitopes in commercial chickens. Importantly, this wild-type *Salmonella* isolate causes no clinically detectable disease or loss of performance in commercial chickens, indicating little disease-causing potential of the wild-type *Salmonella* in vertebrate animals. The ability of an organism to colonize a subject, such as a chicken, is indicated by the ability of the organism to replicate at the site of infection. Optimally, a vaccine candidate can also invade and spread to tissues beyond the infection site. As demonstrated in Example 4, SE13A is capable of replication in the cecal tonsils after oral infection and can be isolated from the tonsils for weeks after infection. In addition, SE13A can invade other tissues, and is found in the liver and the spleen up to a month after infection.

The SE13A isolate may be further attenuated by inactivating at least one gene necessary for sustained replication of the bacteria outside of laboratory or manufacturing conditions. Attenuated *Salmonella* strains that can be used as vaccine vectors are described below. SE13A was used to generate attenuated *Salmonella* strains to develop vaccines and generate enhanced immune responses. As demonstrated in the Examples, SE13A is invasive, non-pathogenic for poultry and causes no measurable morbidity. These features result in an enhanced immune response as compared to non-invasive bacterial vectors. Attenuation of SE13A by mutation of genes that limit the ability of the bacterium to spread may increase the safety of the vaccine. As demonstrated in the Examples at Table 4, SE13A strains with mutations in aroA or htrA retain the ability to generate an immune response, but have limited replication in the host. Thus, the attenuation increases the safety of the vaccine vector without compromising the immunogenicity.

Mutations may be made in a variety of other *Salmonella* genes including, but not limited to, cya, crp, asd, cdt, phoP, phoQ, ompR, outer membrane proteins, dam, htrA or other stress related genes, aro, pur and gua. As shown in the Examples, mutations in aroA and htrA were found to attenuate SE13A. The aro genes are enzymes involved in the shikimate biosynthesis pathway or the aromatase pathway and aro mutants are auxotrophic for the aromatic amino acids tryptophan, tyrosine and phenylalanine. htrA is a stress response gene that encodes a periplasmic protease that degrades aberrant proteins. Mutants in htrA are also attenuated and display increased sensitivity to hydrogen peroxide.

The mutations in aroA and htrA described in the Examples are deletion mutations, but the mutations can be made in a variety of ways. Suitably, the mutations are non-reverting mutations that cannot be repaired in a single step. Suitable mutations include deletions, inversions, insertions and substitutions. A vaccine vector may include more than one mutation, for example a vaccine vector may contain mutations in both aroA and htrA. Methods of making such mutations are well known in the art.

SE13A or the attenuated recombinant SE13A derivatives may be used as vaccine vectors. Polynucleotides encoding polypeptide epitopes from any number of pathogenic organisms may be inserted into the bacteria and expressed by the bacteria to generate antigenic polypeptides. The polynucleotides may be inserted into the chromosome of the bacteria or encoded on plasmids or other extrachromosomal DNA. Suitably, polynucleotides encoding epitopes are inserted into a bacterial polynucleotide that is expressed. Suitably, the bacterial polynucleotide encodes a transmembrane protein, and the polynucleotide encoding the epitope is inserted into the bacterial polynucleotide sequence to allow expression of the epitope on the surface of the bacteria. For example, the polynucleotide encoding the epitope may be inserted in frame into the bacterial polynucleotide in a region encoding an external loop region of a transmembrane protein such that the bacterial polynucleotide sequence remains in frame. See Example 1.

Alternatively, the polynucleotide encoding the epitope may be inserted into a secreted polypeptide. Those of skill in the art will appreciate that the polynucleotide encoding the epitope could be inserted in a wide variety of bacterial polynucleotides to provide expression and presentation of the epitope to the immune cells of a subject treated with the bacterial vaccine vector. In the Examples, an Influenza A virus M2e epitope was inserted into loop 9 of the lamB gene of SE13A and surface expression of the epitope was confirmed by antibody-mediated precipitation. The polynucleotide encoding an epitope may be included in a single copy or more than one copy. In the Examples, a bacterial vaccine vector containing multiple copies of the M2e epitope inserted into loop 9 of lamB is described. Alternatively, multiple copies of an epitope may be inserted into the bacterial vaccine vector at more than one location.

Polynucleotides encoding polypeptides that are homologous to proteins of the subject and capable of stimulating the immune system to respond to the foreign epitope may also be inserted into a vaccine vector. As described in more detail below, a vaccine vector may include a CD154 polypeptide that is capable of binding CD40 in the subject and stimulating the subject to respond to the vaccine vector and its associated foreign epitope. As described above with regard to epitopes, these polynucleotides may be inserted into the chromosome of the vaccine vector or maintained extrachromosomally. One of skill in the art will appreciate that these polypeptides can be inserted in a variety of polynucleotides and expressed in different parts of the vaccine vector or may be secreted. The polynucleotide encoding a CD154 polypeptide capable of enhancing the immune response to a foreign epitope may also encode the foreign epitope. The polynucleotide encoding a CD154 polypeptide may be linked to the polynucleotide encoding the epitope, such that in the vaccine vector the CD154 polypeptide and the foreign epitope are present on the same polynucleotide. In the Examples, a polynucleotide encoding a polypeptide of CD154 that is capable of binding to CD40 also encodes the M2e epitope of Influenza A. See SEQ ID NOS: 8 and 9 in the attached sequence listing. In the Examples, the polynucleotide encoding the M2e epitope and the polynucleotide encoding the CD154 polypeptide are both inserted in loop 9 of the lamB gene. Those of skill in the art will appreciate that bacterial polynucleotides encoding other transmembrane proteins and other loops of the lamB gene may also be used.

The SE13A bacteria may include a polynucleotide encoding a polypeptide of the influenza M2 protein. The ectodomain of the Influenza A virus M2 protein, known as M2e, protrudes from the surface of the virus. The M2e portion of the M2 protein contains about 24 amino acids. The M2e polypeptide varies little from one isolate to the next within a given species. In fact, only a few naturally occurring mutations in M2e have been isolated from infected humans since the 1918 flu epidemic. In addition, influenza viruses isolated from avian and swine hosts have different, yet still conserved, M2e sequences. For reviews of the M2e polypeptide sequences isolated from human, avian and swine hosts see Liu et al., Microbes and Infection 7:171-177 (2005) and Reid et al., J. Virol. 76:10717-10723 (2002) each of which are incorporated herein by reference in its entirety. See also SEQ ID NO: 1-4 in the attached sequence listing.

Suitably a polynucleotide encoding the entire M2e polypeptide may be inserted into the vaccine vector or only a portion may be used. In the Examples, an eight amino acid polypeptide (LM2 having amino acid sequence: EVETPIRN, SEQ ID NO:5 or its variant M2eA having amino acid sequence EVETPTRN, SEQ ID NO:20) was incorporated into SE13A and demonstrated to produce an antibody response after administration to chickens. Suitably, the portion of the M2e polypeptide inserted into the vaccine vector is immunogenic. An immunogenic fragment is a peptide or polypeptide capable of eliciting a cellular or humoral immune response. Suitably, an immunogenic fragment of M2e may be the full-length M2e polypeptide, or suitably may be 20 or more amino acids, 15 or more amino acids, 10 or more amino acids or 8 or more amino acids of the full-length sequence.

Other suitable epitopes for inclusion in an Influenza A vaccine vector include, but are not limited to, polynucleotides encoding polypeptides of the hemagglutinin or the nuclear protein of Influenza A. For example, polynucleotides encoding SEQ ID NO:21, SEQ ID NO:22, SEQ ID NO:23, or SEQ ID NO:24 may be included in a vaccine vector. One of skill in the art will appreciate that any of these sequences may be used in combination with any other epitope and may also be used in conjunction with polypeptides encoding immune stimulatory peptides such as a polypeptide of CD154.

As discussed above, a polynucleotide encoding a polypeptide homologous to a protein of the subject that is capable of enhancing the immune response to the epitope may be included in the vaccine vector. In the Examples, SE13A strains including a polynucleotide encoding a CD154 polypeptide capable of binding to CD40 were demonstrated to enhance the immune response to the M2e epitope as measured by increased antibody production in response to vaccination. Suitably, the CD154 polypeptide is fewer than 50 amino acids long, more suitable fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among the various species. The CD154 sequences of chicken and human are provided in SEQ ID NO: 25 and SEQ ID NO: 26, respectively.

The CD40 binding regions of CD154 have been determined for a number of species, including human chicken, duck, mouse and cattle and are shown in SEQ ID NO: 6, SEQ ID NO: 7, SEQ ID NO:27, SEQ ID NO:28, SEQ ID NO:29, respectively. Although there is variability in the sequences in the CD40 binding region between species, the Examples below indicate that the human CD154 polypeptide was able to enhance the immune response in chickens. Therefore, one may practice the invention using species specific CD154 polypeptides or a heterologous CD 154 polypeptide.

In the Examples, several SE13A recombinant bacteria were generated. In each of the SE13A strains the M2e polypeptide and the CD154 polypeptide were encoded on the same polynucleotide and were in frame with each other and the *Salmonella* polynucleotide in which they were inserted. In alternative embodiments, the CD154 polypeptide and the M2e polypeptide may be encoded by distinct polynucleotides. SE13A aroA M2e contains a deletion in aroA and the LM2-M2e epitope (SEQ ID NO:5) inserted into loop 9 of lamB. SE13A aroA M2e-CD154 is the same as SE13A aroA M2e, but also contains the CD154 peptide (SEQ ID NO:6) inserted in loop 9 of lamB with the M2e epitope (See SEQ ID NO:8). This strain is deposited with the ATCC as deposit number PTA-7872.

SE13A htrA M2E contains a deletion in htrA and has the M2e-LM2 epitope inserted in loop 9 of lamB. SE13A htrA M2E-CD154 has the CD154 peptide inserted in loop 9 of lamB with the M2e epitope (SEQ ID NO:8) and is deposited with the ATCC as strain PTA-7873.

The strain designated as SE13A HM contains SEQ ID NO:9 inserted in loop 9 of lamB. This strain contains multiple copies of two epitopes of M2e, referred to as M2e-LM2 (SEQ ID NO:5) and M2eA (SEQ ID NO:20) and the CD154 polypeptide (SEQ ID NO:6).

In the Examples, the above-described recombinant *Salmonella* strains were demonstrated to produce high, putatively protective antibody titers against the M2e epitope of influenza viruses. Furthermore, expression of the immune-stimulating molecule was shown to further increase antibody titers, confirming functionality of this concept and these particular bacterial vaccine vectors.

Compositions comprising an attenuated *Salmonella* strain and a pharmaceutically acceptable carrier are also provided. A pharmaceutically acceptable carrier is any carrier suitable for in vivo administration. The pharmaceutically acceptable carrier may include water, buffered solutions, glucose solutions or bacterial culture fluids. Additional components of the compositions may suitably include excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying.

Methods of enhancing immune responses in a subject by administering a vaccine vector containing a CD154 polypeptide capable of binding to CD40 and activating CD40 are also provided. The vaccine vector comprising the polynucleotide encoding a polypeptide of CD154 capable of binding to CD40 is administered to a subject in an amount effective to enhance the immune response of the subject to the vaccine. Suitably, the vaccine vector contains a polynucleotide encoding a polypeptide including amino acids 140-149 of the human CD154 polypeptide (SEQ ID NO: 26) or a homolog thereof. Several suitable polypeptides are identified herein. Suitably, the polynucleotide encodes a CD154 polypeptide from the same species as the subject. Suitably, a polynucleotide encoding the polypeptide of SEQ ID NO: 6 is used in human subjects, a polynucleotide encoding the polypeptide of SEQ ID NO: 7 is used in chickens, a polynucleotide encoding the polypeptide of SEQ ID NO: 27 is used in ducks, a polynucleotide encoding the polypeptide of SEQ ID NO:28 is used in mice, and a polynucleotide encoding the polypeptide of SEQ ID NO:29 is used in cows. In the Examples, the human CD154 polypeptide (SEQ ID NO: 6) is used in a chicken vaccine vector and is demonstrated to enhance the immune response to a foreign antigen. Thus other heterologous combinations of CD154 polypeptides and subjects may be useful in the methods of the invention. The CD154 polypeptide may be used to enhance the immune response in the subject to any foreign antigen or antigenic polypeptide present in the vaccine vector. One of skill in the art will appreciate that the CD154 polypeptide could be used to enhance the immune response to more than one antigenic polypeptide present in a vaccine vector.

The polypeptide from CD154 stimulates an immune response at least in part by binding to its receptor, CD40. In the Examples, a polypeptide homologous to the CD154 expressed on immune cells of the subject and which is capable of binding to the CD40 receptor on macrophages and other antigen presenting cells was utilized. Binding of this ligand-receptor complex stimulates macrophage (and macrophage lineage cells such as dendritic cells) to enhance phagocytosis and antigen presentation while increasing cytokine secretions known to activate other local immune cells (such as B-lymphocytes). As such, molecules associated with the CD154 peptide are preferentially targeted for immune response and expanded antibody production.

Potential vaccine vectors for use in the methods include, but are not limited to, *Salmonella* (*Salmonella enteritidis*), *Shigella, Escherichia* (*E. coli*), *Yersinia, Bordetella, Lactococcus, Streptococcus, Vibrio* (*Vibrio cholerae*), *Listeria*, adenovirus, poxvirus, herpesvirus, alphavirus, and adeno-associated virus.

In addition, methods of enhancing an immune response against influenza A and methods of reducing morbidity associated with subsequent Influenza A infection are disclosed. Briefly, the methods comprise administering to a subject a bacterium comprising an Influenza A M2e polynucleotide sequence encoding a polypeptide of Influenza A M2e in an effective amount. The M2e polypeptides include SEQ ID NO:1-5 and 20. The insertion of the M2e polypeptides into the bacterium may be accomplished in a variety of ways known to those of skill in the art, including but not limited to the scarless site-directed mutation system described herein. The bacterium may also be engineered to express the M2e polypeptides in conjunction with polynucleotides capable of enhancing the immune response as discussed above, such as in SEQ ID NO:8 and SEQ ID NO:9. In particular, a polypeptide of CD154 capable of binding CD40 may be expressed by the bacterium to enhance the immune response of the subject to the M2e polypeptide.

The useful dosage to be administered will vary depending on the age, weight and species of the subject, the mode and route of administration and the type of pathogen against which an immune response is sought. The composition may be administered in any dose of bacteria sufficient to evoke an immune response. It is envisioned that doses ranging from $10^3$ to $10^{10}$ bacteria, from $10^4$ to $10^9$ bacteria, or from $10^5$ to $10^7$ bacteria are suitable. The composition may be administered only once or may be administered two or more times to increase the immune response. For example, the composition may be administered two or more times separated by one week, two weeks, or by three or more weeks. The bacteria are suitably viable prior to administration, but in some embodiments the bacteria may be killed prior to administration. In some embodiments, the bacteria may be able to replicate in the subject, while in other embodiments the bacteria may not be capable of replicating in the subject.

For administration to animals or humans, the compositions may be administered by a variety of means including, but not limited to, intranasally, mucosally, by spraying, intradermally, parenterally, subcutaneously, orally, by aerosol or intramuscularly. Eye-drop administration or addition to drinking water or food are additionally suitable. For chickens, the compositions may be administered in ovo.

Some embodiments of the invention provide methods of enhancing immune responses in a subject. A subject includes, but is not limited to, a vertebrate, suitably a mammal, suitably a human, or birds, suitably poultry such as chickens. Other animal models of infection may also be used. Enhancing an immune response includes, but is not limited to, inducing a therapeutic or prophylactic effect that is mediated by the immune system of the subject. Specifically, enhancing an immune response may include enhanced production of antibodies, such as demonstrated in FIG. 3 and FIG. 4, enhanced class switching of antibody heavy chains, maturation of antigen presenting cells, stimulation of helper T cells, stimulation of cytolytic T cells or induction of T and B cell memory.

It is envisioned that several epitopes or antigens from the same or different pathogens may be administered in combination in a single vaccine vector to generate an enhanced immune response against multiple antigens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time. For example, live attenuated bacteria, such as *Salmonella enteritidis* 13A, provide a suitable vaccine vector for eliciting an immune response against multiple antigens.

Heterologous polynucleotides encoding antigens can be inserted in the bacterial genome at any non-essential site or alternatively may be carried on a plasmid using methods well known in the art. One suitable site for insertion of polynucleotides is within external portions of transmembrane proteins or coupled to sequences which target the heterologous polynucleotide for secretory pathways. One example of a suitable transmembrane protein for insertion of polynucleotides is the lamB gene. In the Examples, M2e and CD154 polynucleotides were inserted into loop 9 of the lamB sequence.

Heterologous polynucleotides include, but are not limited to, polynucleotides encoding antigens selected from pathogenic microorganisms or viruses other than the vaccine vector. Such polynucleotides may be derived from pathogenic viruses such as influenza (e.g., M2e, hemagglutinin, or neuraminidase), herpesviruses (e.g., the genes encoding the structural proteins of herpesviruses), retroviruses (e.g., the gp160 envelope protein), adenoviruses, paramyxoviruses, coronaviruses and the like. Heterologous polynucleotides can also be obtained from pathogenic bacteria, e.g., genes encoding bacterial proteins such as toxins, and outer membrane proteins. Further, heterologous polynucleotides from parasites, such as *Eimeria* are attractive candidates for use of a vector vaccine.

Polynucleotides encoding polypeptides involved in triggering the immune system may also be included in a vaccine vector, such as a live attenuated *Salmonella* vaccine. The polynucleotides may encode immune system molecules known for their stimulatory effects, such as an interleukin, Tumor Necrosis Factor or an interferon, or another polynucleotide involved in immune-regulation. The vaccine vector may also include polynucleotides encoding peptides known to stimulate an immune response, such as the CD154 polypeptide described herein.

A method of generating site-specific mutations in a bacterium that is a member of the Enterobacteraciae family is provided. The method as exemplified makes use of overlapping extension PCR, the Red recombinase system, and an intermediary insertion of the I-SceI endonuclease recognition site as a counter-selection marker. Alternatively, sacB may also be used as a counter-selection marker. The overall strategy is shown in FIG. 1. Overlapping extension PCR was used to produce linear DNA with long flanking homology to the genome of SE13A. The Red recombinase system was used to mediate recombination between incoming linear, PCR-generated DNA with the bacterial genome. In the two-step mutation process, the I-SceI site/Km$^r$ cassette was first inserted into the chromosome in the lamB gene by homologous recombination. Then, this mutation was replaced with the desired insertion sequences (LM2-M2e, CD154s or combination sequences). To make the replacement, a PCR product carrying the desired insertion sequence was added simultaneously with a plasmid encoding the I-SceI endonuclease enzyme used for counter-selection between the first and second mutations.

The procedure for generating site-directed mutants may be used in any member of the Enterobacteraciae family. The Enterobacteraciae family includes, but is not limited to, members of the *Salmonella, Shigella, Escherichia* and *Yersinia* genera. A site-directed mutant includes but is not limited to insertion, deletion, substitution and replacement mutations targeted to a specific location in the chromosome of the bacteria. The advantage of the current system is that it results in a "scarless" mutation or a mutation that does not contain any extraneous sequences. Thus, the site-directed mutagenesis disclosed herein can be used to generate autologous bacteria which are deleted for a single gene or even a single amino acid or nucleotide.

In the Examples, the polynucleotides were generated by overlapping extension PCR, but one of skill in the art will appreciate that other methods of generating linear polynucleotides are available and could be utilized. The linear first and second polynucleotides must contain some sequence homologous to the sequence flanking the mutation site to allow for Red mediated recombination. The amount of homologous sequence may comprise less than 300 base pairs on either side of the mutation site. Suitable the homologous sequence is less than 200 base pairs. The polynucleotides may be introduced into the bacteria by any method known to those of skill in the art. In the Examples, the linear polynucleotides were electroporated into the bacteria.

Methods of developing a bacterial vaccine vector are also provided. First, a bacterium capable of colonizing a subject is selected. Then, the bacterium is attenuated to generate an attenuated bacterium. Attenuation may be performed by a variety of methods known to those of skill in the art. Finally, a CD154 polynucleotide sequence encoding a CD154 polypeptide capable of binding CD40 is incorporated into the attenuated bacterium to generate a vaccine vector. The CD154 polypeptide may be fewer than 50 amino acids long and will comprise amino acids 140-149 of CD154 SEQ ID NO: 26 or a homolog thereof. The bacterial vaccine vector may also incorporate a second polynucleotide sequence encoding an antigenic polypeptide. In one embodiment, the CD154 polypeptide and the antigenic polypeptide are encoded on the same polynucleotide sequence.

The following examples are meant only to be illustrative and are not meant as limitations on the scope of the invention or of the appended claims.

EXAMPLES

Example 1. Construction of M2e and M2e/CD154 Inserts

Strains and Culture Conditions

All plasmids were first maintained in TOP10 *E. coli* cells (Invitrogen, Carlsbad, Calif., USA) unless described otherwise. *Salmonella enteritidis* 13A was used for introduction of mutations. *Salmonella enteritidis* strain 13A was a field isolate available from USDA/APHIS/NVSL and deposited with the ATCC as deposit number PTA-7871. Bacteria carrying plasmid pKD46 were grown at 30° C. Other bacteria were grown at 37° C. Plasmid curing was conducted at 37° C.

Luria-Bertani (LB) media was used for routine growth of cells, and SOC media (Invitrogen, Carlsbad, Calif., USA) was used for phenotypic expression after electroporation. When appropriate, the following antibiotics were added to the media: ampicillin (Amp) at 100 µg/ml, kanamycin (Km) at 50 µg/ml, and chloramphenicol (Cm) at 25 µg/ml.

Plasmids

Plasmids pKD46, pKCD13, and pBC-I-SceI were described previously (Datsenko and Wanner, PNAS 2000, 97:6640-6645 and Kang et al., J Bacteriol 2004, 186:4921-4930, both of which are incorporated herein by reference in their entireties). Plasmid pKD46 encodes Red recombinase enzymes which mediate homologous recombination of incoming linear DNA with chromosomal DNA. This plasmid also contains the Ampicillin resistance gene and is temperature-sensitive so that it requires 30° C. for maintenance in the cell. Plasmid pKD13 served as a template for amplification of the Km resistance (Km$^r$) gene used in overlapping PCR. Plasmid pBC-I-SceI, which is maintained in the cell at 37° C., produces the I-SceI enzyme, which cleaves the following 18 base pair, rare recognition sequence: 5'-TAGGGATAACAGGGTAAT-3' (SEQ ID NO:30). Plasmid pBC-I-SceI also contains the chloramphenicol resistance (Cm$^r$) gene.

PCR

All primers used for PCR are listed in Table 1. Typically, PCR was performed using approximately 0.1 µg of purified genomic, plasmid or PCR-generated DNA (Qiagen, Valencia, Calif., USA), 1× cloned Pfu polymerase buffer, 5 U Pfu polymerase (Stratagene La Jolla, Calif., USA), 1 mM dNTPs (GE Healthcare Bio-Sciences Corp., Piscataway, N.J.), and 1.2 µM of each primer in a total volume of 50 µL. The DNA engine thermal cycler (Bio-Rad, Hercules, Calif., USA) was used with the following amplification conditions: 94° C. for 2 minutes; 30 cycles of 94° C. sec for 30 sec, 58° C. for 60 sec, 72° C. for 90 sec per 1 kb; and 72° C. for 10 minutes for final extension. Each PCR product was gel purified (Qiagen, Valencia, Calif., USA) and either eluted in 25 µL EB buffer for preparation of templates used in overlapping extension PCR or in 50 µL EB buffer, ethanol precipitated and suspended in 5 µL of ddH$_2$O for electroporation into *S. enteritidis*.

TABLE 1

Primer sequences

| Primer | Amplified region | Primer sequence |
|---|---|---|
| lam-up-f | loop 9 up | 5'TGTACAAGTGGAC GCCAATC 3' (SEQ ID NO: 10) |
| lam-up-r | | 5'*GTTATCGCCGTCT TTGATATAGCC* 3' (SEQ ID NO: 11) |
| lam-dn-f | looop 9 dn | 5'*ATTTCCCGTTATG CCGCAGC* 3' (SEQ ID NO: 12) |
| lam-dn-r | | 5'GTTAAACAGAGGG CGACGAG 3' (SEQ ID NO: 13) |
| Km-f | I-SceI/Km$^r$ gene | 5'*GCTATATCAAAGA CGGCGATAAC*TAACT ATAACGGTCCTAAGG TAGCGAATTTCCGGG GATCCGTCGA 3' (SEQ ID NO: 14) |
| Km-r | | 5'*GCTGCGGCATAAC GGGAAATTGTAGGCT GGAGCTGCTTCG* 3' (SEQ ID NO: 15) |
| Kan4f | inside Km$^r$ gene: sequencing | 5'CAAAAGCGCTCTG AAGTTCC 3' (SEQ ID NO: 31) |
| Kan4r | | 5'GCGTGAGGGGATC TTGAAGT 3' (SEQ ID NO: 32) |
| lam-i1 | M2e/loop 9 dn | 5'*GCTATATCAAAGA CGGCGATAAC*<u>GAAGT TGAAACCCCGATTCG TAAC</u>*ATTTCCCGTTA TGCCGCAGCG* 3' (SEQ ID NO: 16) |
| lam-i2 | CD154s/loop 9 dn | 5'*GCTATATCAAAGA CGGCGATAAC*<u>TGGGC AGAAAAAGGTTATTA TACCATGTCTATTTC</u> *CCGTTATGCCGCAG C* 3' (SEQ ID NO: 17) |

TABLE 1-continued

Primer sequences

| Primer | Amplified region | Primer sequence |
|---|---|---|
| i2-i1h-f | CD154s-(Gly)$_3$-LM2-(Gly)$_3$-loop 9 dn | 5'<u>TGGGCAGAAAAAG GTTATTATACCATGT CTGGTGGTGGTGAAG TTGAAACCCCGATTC GTAAC</u>GGTGGTGGTA *TTTCCCGTTATGCCG CAGC* 3' (SEQ ID NO: 33) |
| i2-i1-r | CD154s-(Gly)$_3$-loop 9 up | 5'<u>AGACATGGTATAA TAACCTTTTTCTGCC CAACCACCACCGTTA</u> *TCGCCGTCTTTGATA TAGCC* 3' (SEQ ID NO: 34) |
| TJ1-f | CD154-(Ser)$_4$-LM2-(Ser)$_4$-LM2-(Ser)$_4$-loop 9 dn | 5'<u>TGGGCAGAAAAAG GTTATTATACCATGT CTTCCTCCTCCTCCG AAGTTGAAACCCCGA TTCGTAACTCCTCCT CCTCCGAAGTTGAAA CCCCGATTCGTAACT CCTCCTCCTCCATTT</u> *CCCGTTATGCCGCAG C* 3' (SEQ ID NO: 35) |
| TJ1-r | CD154-(Ser)$_4$-M2eA-(Ser)$_4$-M2eA-(Ser)$_4$-loop 9 up | 5'<u>AGACATGGTATAA TAACCTTTTTCTGCC CAGGAGGAGGAGGAG TTACGGGTCGGGGTT TCAACTTCGGAGGAG GAGGAGTTACGGGTC GGGGTTTCAACTTCG GAGGAGGAGGAGTTA</u> *TCGCCGTCTTTGATA TAGCC* 3' (SEQ ID NO: 36) |
| lam 3f | outer regions of loop 9: sequencing | 5'GCCATCTCGCTTG GTGATAA 3' (SEQ ID NO: 18) |
| lam 3r | | 5'CGCTGGTATTTTG CGGTACA 3' (SEQ ID NO: 19) |

In Table 1, italicized nucleotides are complementary to either side of the lamB gene loop 9 insertion site, which corresponds to nucleotide 1257 using *S. typhimurium* as an annotated reference genome. Bold font nucleotides represent the I-SceI recognition site in the Km-f primer. All other insertion sequences are shown as underlined.

Electroporation

Transformation of pKD46 into *S. enteritidis* was the first step carried out so that Red recombinase enzymes could be used for mediating recombination of subsequent mutations. Plasmid pKD46 was harvested from *E. coli* BW25113 (Datsenko and Wanner, PNAS 2000, 97:6640-6645) using a plasmid preparation kit (Qiagen Valencia, Calif., USA). Then 0.5 µL of pKD46 DNA was used for transformation into *S. enteritidis* 13A which had been prepared for electroporation. (Datsenko and Wanner, PNAS 2000, 97:6640-6645). Briefly, cells were inoculated into 10-15 mL of 2×YT broth and grown at 37° C. overnight. Then 100 µL of overnight culture was re-inoculated into 10 mL fresh 2×YT broth at 37° C. for 3-4 hours. Cells to be transformed with pKD46 plasmid were heated at 50° C. for 25 minutes to help inactivate host restriction. Cells were washed five times in $ddH_2O$ water and resuspended in 60 µL of 10% glycerol. Cells were then pulsed at 2400-2450 kV for 1-6 ms, incubated in SOC for 2-3 hours at 30° C. and plated on LB media with appropriate antibiotics. *S. enteritidis* transformants with pKD46 were maintained at 30° C. When these transformants were prepared for additional electroporation reactions, all steps were the same except that 15% arabinose was added to induce Red recombinase enzymes one hour prior to washing, and cells did not undergo the 50° C. heat step.

Loop 9 Up-I-SceI/$Km^r$-Loop 9 Down Construct

Figure 2:
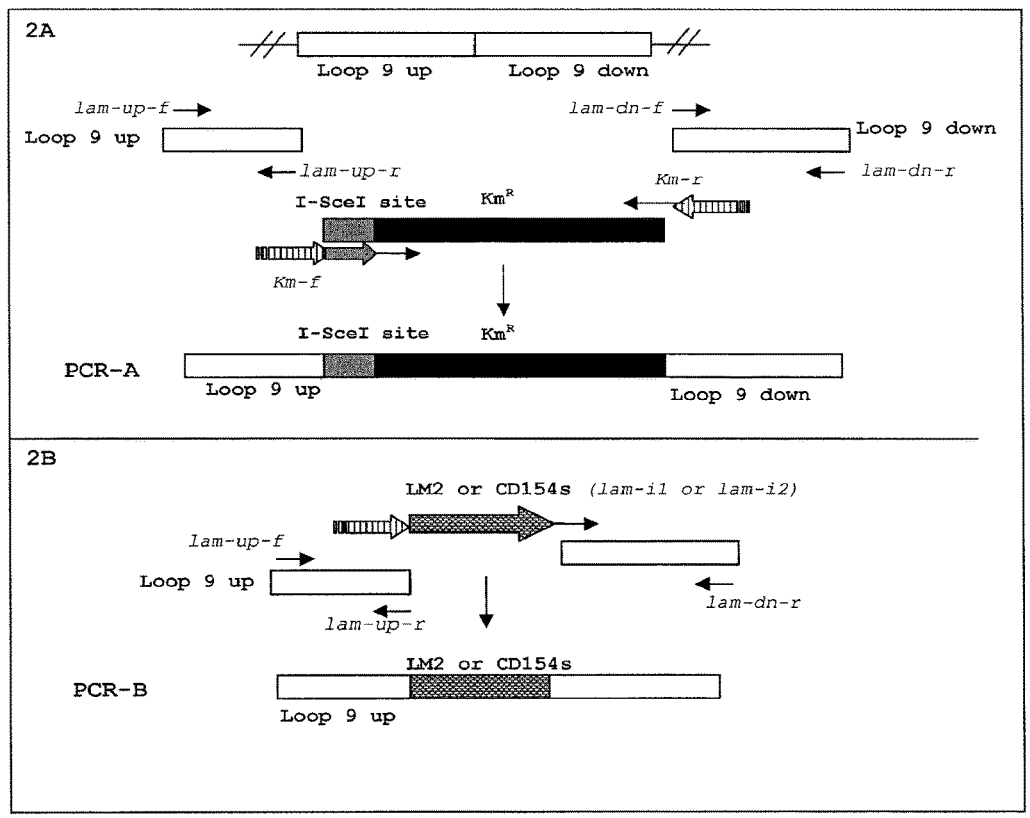
FIG. 2 depicts the design scheme of the overlapping extension PCR method used to generate the M2e and M2e-CD154 insertions into loop 9 of the lamB polynucleotide.
Figure 3:
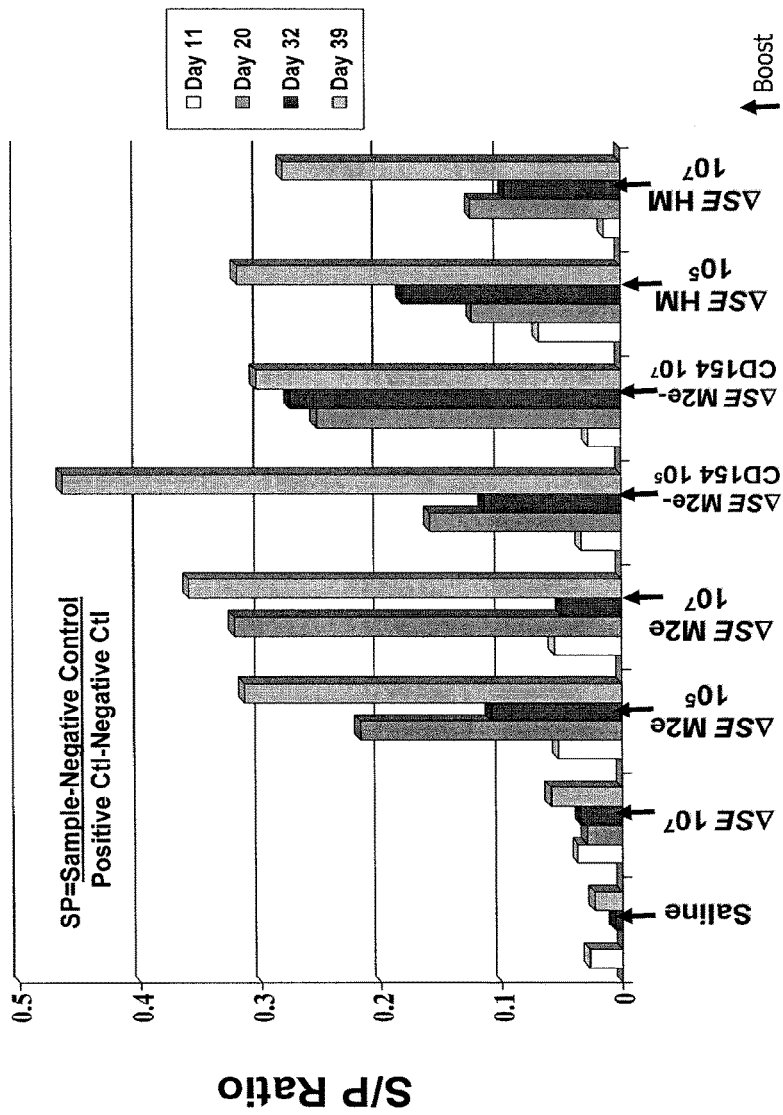
FIG. 3 is a bar graph showing the relative amount of serum antibody generated at the time points indicated in response to administration of the indicated treatment.
Figure 4:
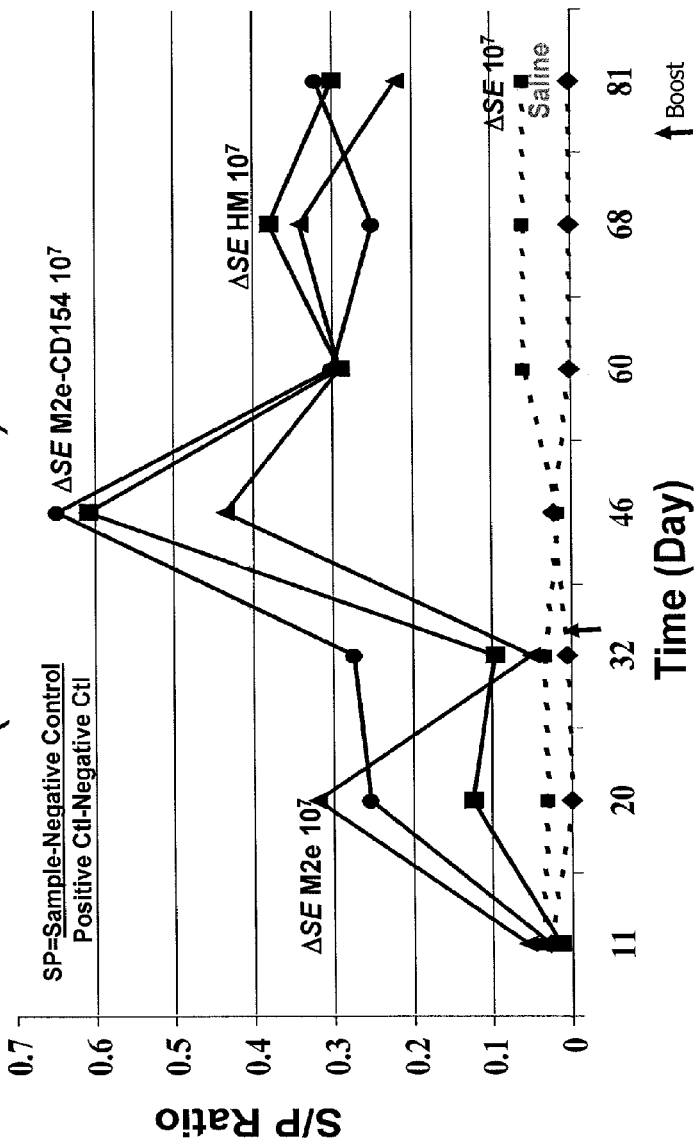
FIG. 4 is a line graph showing the amount of serum antibody over time after administration of the indicated treatments.

Introduction of I-SceI enzyme recognition site along with the $Km^r$ gene into loop 9 of the lamB gene was done by combining the Red recombinase system (Datsenko and Wanner, PNAS 2000, 97:6640-6645, which is incorporated herein by reference in its entirety) and overlapping PCR (Horton et al., BioTechniques 1990, 8:528-535, which is incorporated herein by reference in its entirety). The insertion site corresponds to nucleotide 1257 of the lamB gene using *Salmonella typhimurium* LT2 (*S. typhimurium*) as an annotated reference genome. First, the upstream and downstream regions immediately flanking the loop 9 insertion site (loop 9 up and loop 9 down, respectively) were amplified separately. Primers used were lam-up-f and lam-up-r for loop 9 up and lam-dn-f and lam-dn-r for loop 9 down. Then the $Km^r$ gene from pKD13 plasmid was amplified using primers Km-f and Km-r. Here, the I-SceI enzyme site was synthetically added to the 5' end of Km-f primer then preceded by a region complimentary to the loop-up-r primer. Likewise, a region complimentary to the loop-dn-f primer was added to the 5' end of Km-r primer. The complimentary regions allow all 3 PCR products to anneal when used as templates in one PCR reaction. FIG. 2A represents this design scheme. PCR fragments consisting of loop 9 up-I-SceI/$Km^r$-loop 9 down sequence (PCR-A) were electroporated into *S. enteritidis* cells, which harbored pKD46 and were induced by arabinose, and then plated on LB with Km plates. To verify the correct sequence orientation of the mutation, we performed colony PCR with primer pairs Kan4F/lam3f and Kan4R/lam3r, where Kan4F and Kan4R are $Km^r$ gene-specific primers and lam3f and lam3r are primers located outside the lamB loop 9 region. These PCR fragments were gel purified (Qiagen, Valencia, Calif., USA) and used for DNA sequencing.

Loop 9 Up-LM2 or CD154s or Combination Sequence—Loop 9 Down Construct

The final overlapping PCR fragment, PCR-B, contained the added LM2 (or CD154s or combination sequences flanked by loop 9 up and down regions (FIG. 2B). Combination sequences consisted of LM2 or an alternate M2e epitope associated with avian species (M2eA) and CD154 along with spacers such as Glycine (Gly) or Serine (Ser) residues. Inserted sequences were as follows: LM2 (SEQ ID NO:37); M2eA (SEQ ID NO:38); combination sequence no. 1 $(Gly)_3$-CD154s-$(Gly)_3$-LM2-$(Gly)_3$ (SEQ ID NO:39); and combination sequence no. 2 $(Ser)_4$-M2eA-$(Ser)_4$-M2eA-$(Ser)_4$-CD154-$(Ser)_4$-LM2-$(Ser)_4$-LM2-$(Ser)_4$ (SEQ ID NO:40).

To shorten the amount of steps for construction of the next fragment, the LM2 or CD154 sequence was synthetically added to the 5' end of the lam-dn-f primer and preceded by the complimentary region to the loop-up-r primer. The previously used PCR product for loop 9 up could be used together with the newly constructed PCR product in which LM2 or CD154s were incorporated at the 5' end of loop 9 down to perform the final PCR reaction. However, for other insert sequences (referred to as combination sequences), an extra PCR step was needed, due to the longer lengths of insert sequences, to amplify loop 9 up with added nucleotides specific to insertion sequences connected to loop-up-r primer. The coding sequence for Gly (GGT) and Serine (TCC) as well as all other amino acids were chosen based on compiled data of the most frequently used codons in *E. coli* and *Salmonella typhimurium* proteins. See Table 1 for further details of primer design.

Genomic Replacement of I-SceI/$Km^r$ with LM2 or CD154s or Combination Sequences PCR-B products were electroporated into *S. enteritidis* cells along with plasmid pBC-I-SceI at a molar ratio of approximately 40:1 (Kang et al., J Bacteriol 2004, 186: 4921-4930, which is incorporated herein by reference in its entirety). Clones for each PCR-B recombination mutation were chosen according to the ability to grow on Cm plates but not on Km plates, due to the replacement of PCR-B for the $Km^r$ encoding PCR-A sequence. Modified regions in the selected clones were PCR-amplified, and DNA sequences were determined using primers lam3f and lam3r located outside the loop 9 down and up amplified regions.

I-SceI site/$Km^r$ Insertion Mutation

The first mutation step involved designing a PCR fragment, PCR-A, which would serve as the carrier of the I-SceI site/$Km^r$ cassette to be inserted into the lamB site. PCR-A consisted of the I-SceI enzyme recognition site adjacent to the $Km^r$ gene with approximately 200-300 bp of flanking DNA on each end homologous to the upstream and downstream regions of lamB loop 9 insertion site (loop 9 up and loop 9 down, respectively). The fragment was introduced into *S. enteritidis* cells expressing Red recombinase enzymes and $Km^r$ colonies were selected. After screening a few colonies by colony PCR, positive clones were sequenced for the desired inserted I-SceI site/$Km^r$ sequence, and the identified mutant was designated SE164.

Genomic Replacement of I-SceI/$Km^r$ with LM2 or CD154s or Combination Sequences The second mutation step required constructing a PCR fragment, referred to as PCR-B and shown in FIG. 2B, consisting of the final insertion sequence, LM2 or CD154 or combination sequences, flanked by lamB homologous fragments. PCR-B amplicons have no selection marker and must be counter-selected after replacement for the previous I-SceI site/$Km^r$ mutation in SE164. Plasmid pBC-I-SceI encodes the $Cm^r$ gene and the I-SceI enzyme, which will cut the genome at the I-SceI site of SE164. Therefore, pBC-I-SceI was electroporated into SE164 along with PCR-B. After recombination of PCR-B to replace PCR-A, positive clones were chosen based on the ability to grow on Cm but not on Km. After DNA sequencing of mutants to confirm successful recombination of PCR-B, the strains were designated SE172, SE173, SE180, and SE189 for insert sequences LM2, CD154s, $(Gly)_3$-CD154s-$(Gly)_3$-LM2-$(Gly)_3$ (SEQ ID NO: 39), and $(Ser)_4$-M2eA-$(Ser)_4$-M2eA-$(Ser)_4$-CD154-$(Ser)_4$-LM2-$(Ser)_4$-LM2-$(Ser)_4$ (SEQ ID NO: 40), respectively. Ten random clones for each the LM2 and CD154s insertion were used for PCR with lam 3f and lam 3r then digested using unique restriction enzymes sites for each insertion sequence and 100% of clones tested by digestion were positive for the desired mutation sequence. Sequencing results demonstrated that the insertion of LM2 or CD154s or combination sequences was exactly into the loop 9 region without the addition of extraneous nucleotides.

Example 2. Attenuation of M2e or M2e/CD154 Mutants/Inserts

Attenuation of SE13A was achieved by deletion mutation of the aroA gene and/or the htrA gene. Mutation of the aroA gene, a key gene in the chorismic acid pathway of bacteria, results in a severe metabolic deficiency which affects seven separate biochemical pathways. Mutation of the htrA gene reduces the cell's ability to withstand exposure to low and high temperatures, low pH, and oxidative and DNA damaging agents and reduces the bacteria's virulence.

To achieve deletion mutations in SE13A, the target gene sequence in the bacterial genome of *S. enteritidis* was replaced with the Km resistant gene sequence. This was completed using overlapping extension PCR and electroporation of the PCR products as described above. The Km resistance gene was targeted into the genomic region containing the genes of interest (aroA or htrA) by flanking the Km resistance gene with 200-300 base pairs of sequences homologous to the genes of interest. Once Km resistant mutants were obtained, the aroA or htrA deletion mutations were confirmed by DNA sequencing. The resulting aroA- and htrA-*Salmonella* strains were deposited with the American Type Culture Collection on Sep. 13, 2006 (Deposit No. PTA-7872 and Deposit No. PTA-7873, respectively). The attenuated strains were also tested in vivo with regards to clearance time. Both of the attenuated strains had quicker clearance times than did the wildtype 13A strain, but both were able to colonize the liver, spleen, and cecal tonsils of chickens after oral infection. In addition, an attenuated strain lacking both aroA and htrA was also isolated.

Example 3. Confirmation of Cell Surface Expression of M2e and CD154

Cell surface expression of the M2e and CD154 inserts was confirmed with a simple antibody/antigen precipitation reaction. In short, polyclonal antibodies were made against the amino acid sequences of both M2E-LM2 (EVETPIRN; SEQ ID NO:5) and CD154 (WAEKGYYTMSC; SEQ ID NO:6) conjugated to a carrier protein (KLH). The resulting antibodies were then incubated with SE13A wildtype (no inserts) or SE13A with either the M2e-LM2, the CD154 or the M2e-LM2 and CD154 combined insert on a glass plate at room temperature and allowed to incubate for 30 seconds. Cell surface expression was determined by the presence of a precipitate. Results are shown in Table 2. A positive precipitation reaction is indicated by a (+) sign and a negative precipitation reaction is indicated by a (−) sign. The results demonstrate that the SE13A wildtype did not react with the M2e and CD154 peptide antibodies, while the strains expressing M2e, CD154 or M2e and CD154 reacted with the appropriate antibodies. Thus, M2e and CD154 peptides are being expressed on the surface of the bacteria.

TABLE 2

| | Precipitation reaction | | | |
|---|---|---|---|---|
| | SE13A | SE13A-M2E | SE13A-CD154 | SE13A-M2E-CD154 |
| M2E antibody | − | + | Not tested | + |
| CD154 antibody | − | Not tested | + | + |

Example 4. Vaccination Study

Day-of-hatch (day 0) chicks were obtained from a local commercial hatchery and randomly distributed into treatment groups (n=55/treatment group). Fifteen chicks out of the possible 55 in each treatment group were tagged and numbered. The chicks were orally infected by gavage with 0.25 ml of $10^4$, $10^5$, or $10^7$ (data not shown) cfu/ml of the various SE13A treatments as indicated in Table 3.

TABLE 3

Challenge Dose for each treatment group.

| Treatment Group | Challenge Dose |
|---|---|
| SE13A-M2E | $10^5$ cfu/ml |
| SE13A-M2E-CD154 | $10^5$ cfu/ml |
| SE13A-M2E aroA | $10^4$ cfu/ml |
| SE13A-M2E-CD154 aroA | $10^4$ cfu/ml |
| SE13A-M2E htrA | $10^5$ cfu/ml |
| SE13A-M2E-CD154 htrA | $10^5$ cfu/ml |

Each treatment group was housed in an individual floor pen on fresh pine litter and provided water and feed ad libitum. On days 7, 14, 21 and 28 post-hatch, approximately 1 ml of blood was collected from each of the fifteen tagged birds and the serum was removed for later use in determining antibody titers. On the same days, ten birds from each treatment group were euthanized, their liver, spleen and ceca tonsils aseptically removed for determination of bacterial colonization (ceca tonsils) and bacterial invasion (liver and spleen). Individual liver, spleen and ceca tonsil samples were pre-enriched in tetrathionate broth overnight at 37° C. The next day loopfuls of each broth culture were streaked onto XLD agar plates supplemented with Novabicin and Naladixic Acid and incubated overnight at 37° C. The following morning the plates were read for the presence or absence of *Salmonella* colonies. Bacterial colonization and invasion data are presented in Table 4 by treatment group. Each ratio presented in Table 4 represents the number of birds from which *Salmonella* positive isolates were recovered out of the possible ten birds that were cultured on days 7, 14, 21, and 28 post-challenge.

TABLE 4

Bacterial Colonization and Invasion.

| | Colonization (Ceca Tonsils) | | | | Invasion (Liver/Spleen) | | | |
|---|---|---|---|---|---|---|---|---|
| Treatment Groups | D7 | D14 | D21 | D28 | D7 | D14 | D21 | D28 |
| SE13A | 9/10 | 3/10 | 5/10 | 2/10 | 8/10 | 8/10 | 2/10 | 4/10 |
| SE13A-M2E-CD154 | 9/10 | 7/10 | 6/10 | 9/10 | 8/10 | 1/10 | 5/10 | 4/10 |
| SE13A-M2E aroA | 10/10 | 4/10 | 0/10 | 3/10 | 9/10 | 4/10 | 0/10 | 3/10 |
| SE13A-M2E-CD154 aroA | 4/10 | 1/10 | 1/10 | 3/10 | 4/10 | 0/10 | 0/10 | 3/10 |
| SE13A-M2E htrA | 5/10 | 1/10 | 0/10 | 1/10 | 4/10 | 2/10 | 0/10 | 2/10 |
| SE13A-M2E-CD154 htrA | 4/10 | 1/10 | 0/10 | 0/10 | 6/10 | 0/10 | 0/10 | 0/10 |

Positive *Salmonella* bacterial isolates recovered from birds in each treatment group were subjected to analysis by polymerase chain reaction (PCR) using the primers specific to each insert disclosed in Table 1 to verify the M2e- and or CD154 insert. This technique was utilized to ensure that the strain that the birds were originally given was equivalent to the strain recovered. In each treatment group, PCR confirmed that the recovered strains were the same as the strains with which the birds were infected. The results indicated acceptable colonization of tissues with the various *Salmonella* strains tested.

Example 5. M2e Antibody Production

Serum collected from the tagged birds in each treatment group was used in an antigen capture ELISA to calculate M2e antibody levels. In brief, individual wells of a 96-well plate were coated with 5 μg/ml of the M2e-LM2 epitope (EVETPIRN: SEQ ID NO:5) conjugated to BSA. Antigen adhesion was allowed to proceed overnight at 4° C. Plates were rinsed with PBS+0.05% Tween 20 and incubated for 2 hours with the serum previously collected from the birds in each of the 6 treatment groups described above. The plates were rinsed with PBS+0.05% Tween 20 followed by incubation with peroxidase conjugated Goat-anti-Chicken IgY secondary antibody (1:10,000 dilution) obtained from Jackson ImmunoResearch Laboratories (West Grove, Pa.) for an additional hour. After subsequent rinsing, the plates were developed using a peroxidase substrate kit obtained from Fisher Scientific and absorbances read on a spectrophotometer at 450 nm and 405 nm.

Each plate also contained a positive control and negative control where the M2e polyclonal antibody described above and chicken serum from an untreated bird respectively replace the serum from the treatment groups. The absorbances obtained for the positive control, negative control and experimental samples were used to calculate Sample to Positive control ratios (S/P ratios) using the following calculation:

$$S/P \text{ ratio calculation: } \frac{\text{sample mean} - \text{negative control mean}}{\text{positive control mean} - \text{negative control mean}}$$

The calculated SIP ratios for each group are shown in FIGS. 3 and 4. As is shown, M2e-specific antibody levels for each group expressing M2e-CD154 produced an ELISA signal that was on average over 30% higher when compared with their respective group that only expresses M2e. The data demonstrate that SE13A-M2e and SE13A-M2e-CD154 are both capable of eliciting a robust antibody response to M2e. This response was clearly augmented by addition of the CD154 peptide. In addition, similar responses were generated when either the aroA or htrA auxotrophic SE13A strains were utilized. These strains may provide vaccine vectors with higher safety for clinical use without sacrificing generation of a robust immune response.

Example 6. Virus Neutralization

Antisera (collected 2 weeks after the booster immunization in each experiment) generated against the recombinant SE vectors described above were subjected to virus neutralization testing using H9N2 Influenza (Charles River Laboratories, Franklin, Conn.) using standard protocols (Charles River Laboratories). See Table 5. Neutralizing indices indicate that the antisera from vaccinated chickens were effective in neutralizing Avian Influenza and thus in protecting embryos from the virus (VN titers ranged from 6.3 to 8.8 in two studies). Hyperimmune serum raised against synthetic M2e peptide was used as a positive control.

TABLE 5

| Virus Neutralization | |
|---|---|
| SE strain | Neutralization Index |
| SE aroA M2E | 7.5 |
| SE aroA M2E-CD154 | 8.3 |
| SE aroA M2E (multi-copy)-CD154 | 8.3 |
| Positive control | 8.3 |

Example 7. Challenge Study

Viruses.

The influenza viruses used in these studies were A/Turkey/Virginia/158512/2002 (TV/02) H7N2 LP Avain Influenza (LPAI H7N2) and A/Egret/Hong Kong/757.2/2002 (Eg/02) H5N1 HP avian influenza (HPAI H5N1). Viruses were grown and titered in 9-11 day old embryonated SPF (specific pathogen free) chicken eggs as previously described (Suarez et al., J Virol. 1998 August; 72(8):6678-88.).

Chickens and Housing.

For LP and HPAI challenge chickens were transferred into negative-pressure-stainless steel Horsfall units containing HEPA filters in a USDA-certified biosafety level 3 agriculture facility. Feed and water were provided ad libitum.

Serology and Virus Isolation.

Hemagglutination inhibition test was performed with BPL-inactivated homologous H5N1 antigen with sera collected at day 0 in Expt. I and Day 0 and 14 in Expt. II as previously described (Suarez et al., 1998). Titers greater ≥3 ($\log_2$) were considered positive. Virus isolation from oral and cloacal swabs on days 2 and 4 post-challenge was performed in 9-11 day of embryonation SPF chicken eggs as previously described (Tumpey et al., Avian Dis. 2004 January-March; 48(1):167-76). Briefly, swabs were collected into 2 ml brain-heart infusion (BHI) broth with antibiotics (1000 units/ml penicillin G, 200 μg/ml gentamicin sulfate, and 4 μg/ml amphotericin B; Sigma Chemical Company, St. Louis, Mo.) from each bird on day 0, 2, 4, days post challenge for virus isolation.

Western Blot.

Purified AIV proteins from whole virus (H5N1 and H7N2) were separated by SDS-PAGE in a 10% polyacrylamide gel and transferred as previously described (Kapczynski and Tumpey, Avian Dis. 2003 July-September; 47(3):578-87). Briefly, anti-M2e serum from birds previously immunized with ΔSE M2e-HM (1:1000) was incubated with the membrane containing AIV antigen for 1 hour at room temperature. Following three washes in PBS-Tween 20 (0.05%) the membrane was reacted with horseradish peroxidase-labeled goat anti-chicken IgG secondary antibody (Southern Biotech Associates, Inc, Birmingham, Ala.) at a 1:2000 dilution for 1 hour. After washing as above, the membrane was reacted with ECL Western Blotting Detection Reagents (Amersham Biosciences, Piscataway, N.J.) according to the manufacturers' recommendations, and exposed to Hyperfilm ECL (Amersham Biosciences). The film was developed using Kodak GBX developing reagents (Eastman Kodak Company) according to the manufacturers' recommendations.

Protection Studies.

The initial experimentation was designed to assess protection of chickens receiving vaccination with ΔSE M2e-HM (multi-copy M2e-CD154 with the SEQ ID NO:9 insertion sequence) *Salmonella* from challenge with LPAI TV/02 ($10^6$ $EID_{50}$ per bird (EID refers to embryo infectious dose)) to determine reduction of morbidity and viral shedding. Subsequently, protection from HPAI Eg/02 challenge was investigated using a sublethal (0.1 $CLD_{50}$ per bird (CLD refers to chick lethal dose)) and lethal dose (100 $CLD_{50}$ per bird), in terms of morbidity, mortality and viral shedding.

Experiment I. Challenge with LPAI H7N2

Figure 5:
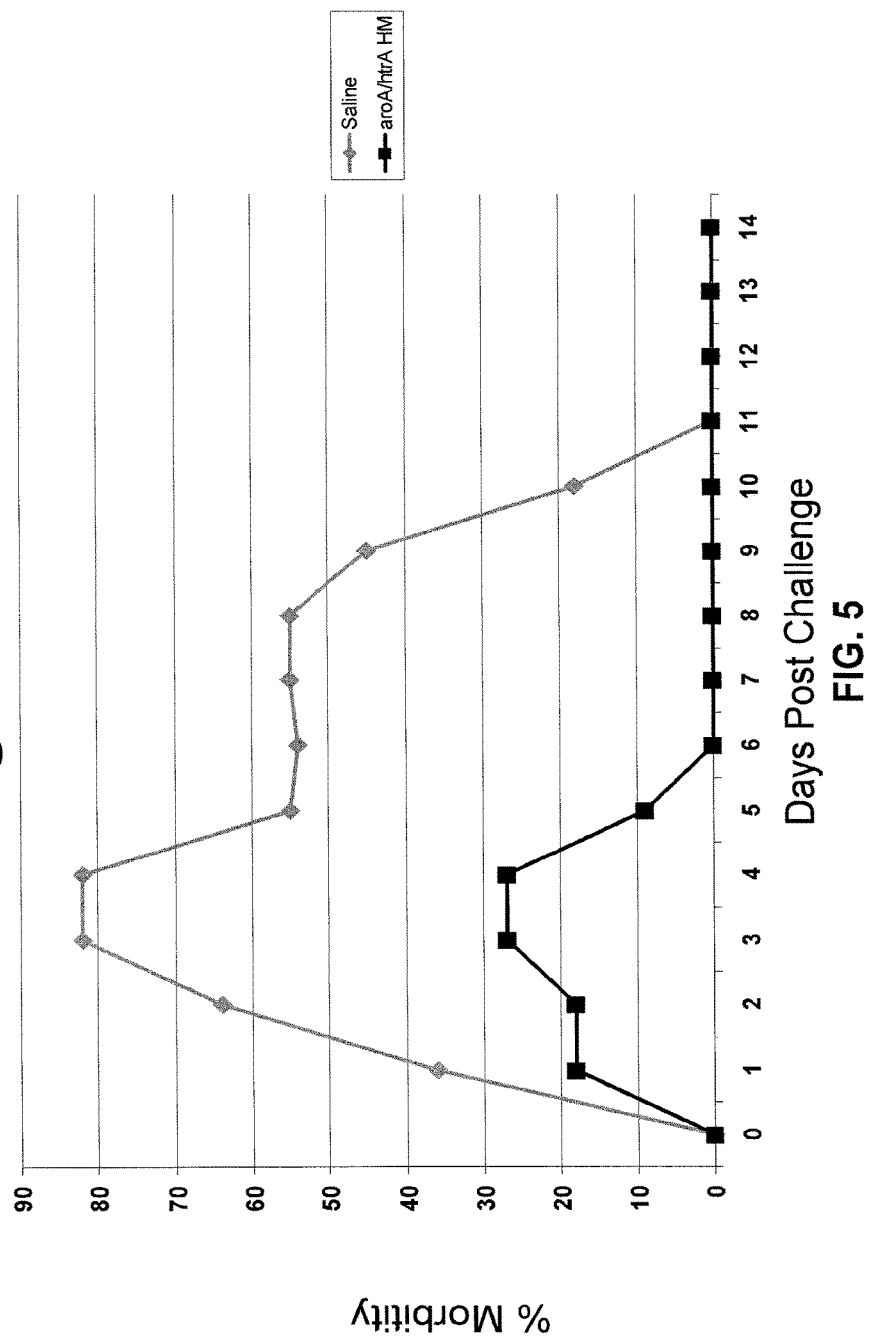
FIG. 5 is a graph showing the morbidity of chickens after vaccination with SE HM at day-of-hatch, boost at day 21 and challenge infection with a low pathogenicity Influenza A at 32 days post-hatch.

Groups of ten 1-day old SPF chickens were divided into 3 groups. Birds in groups 1 and 2 received sham vaccination with 100 µl of phosphate-buffered saline (PBS, pH 7.4). Birds in group 3 received vaccination with ΔSE M2e-HM. Three weeks later (Day 21) the three groups of SPF chickens received an identical second vaccination (boost) utilizing saline (Groups 1 and 2) or the recombinant *Salmonella* vectored vaccine (Group 3). Three weeks after boost (Day 42), birds in group 2 and 3 were challenged intranasally (IN) with $10^6$ embryo infectious dose 50 ($EID_{50}$)/bird of TV/02 (LPAI H7N2). Unchallenged birds were sham-challenged with 100 µl PBS via intranasal route. Following challenge, birds were monitored daily for disease signs for 14 days post-infection (PI). The morbidity results following challenge with LPAI H7N2 are shown in FIG. 5 and demonstrate a significant reduction in morbidity after vaccination with SE13A expressing M2E and CD154. For determining incidence of viral shedding, oral and cloacal swabs were taken on day 2 and 4 PI. The amount of viral shedding following challenge with LPAI H7N2 at days 2 and 4 PI is shown in FIG. 6 and demonstrated that vaccination with SE13A-HM also reduce the ability of AI to replicate in the chicks.

Experiment II. Challenge with HPAI H5N1

Groups of ten 1-day old SPF chickens were divided into 5 groups. Birds in groups 1, 2 and 3 received sham vaccination with 100 µl of phosphate-buffered saline (PBS, pH 7.4). Birds in group 4 and 5 received vaccination with ΔSE M2e-HM as described in Expt. I. On day 42, birds in group 1 receive sham challenge with 100 µl PBS via intranasal route. Birds in groups 2 and 3 received challenge with 0.1 and 100 $CLD_{50}$ Eg/02 (HPAI H5N1) per bird, respectively. Birds in groups 4 and 5 received challenge with 0.1 and 100 $CLD_{50}$ Eg/02 (HPAI H5N1) per bird, respectively. Following challenge, birds were monitored daily for morbidity and mortality for 14 days PI. Chickens displaying severe clinical signs of disease were euthanized by overdose of sodium pentobarbital. The morbidity results following challenge with HPAI H5N1 are shown in FIG. 7 and demonstrate a significant reduction in morbidity after vaccination with SE13A expressing M2E and CD154. For determining incidence of viral shedding, oral and cloacal swabs were taken on day 2 and 4 PI. The amount of viral shedding following challenge with HPAI H5N1 at days 2 and 4 PI is shown in FIG. 8 and demonstrated that vaccination with SE13A-M2e also reduce the ability of AI to replicate in the chicks.

We claim:

1. A vaccine vector comprising a first polynucleotide sequence encoding an antigenic polypeptide and a CD154 polynucleotide sequence encoding a CD154 polypeptide capable of binding CD40, wherein the CD154 polypeptide is expressed on the surface of the vaccine vector.

2. The vaccine vector of claim 1, wherein the antigenic polypeptide is expressed on the surface of the vaccine vector.

3. The vaccine vector of claim 2, wherein the first polynucleotide and the CD154 polynucleotide are inserted into a third polynucleotide encoding an external portion of a transmembrane protein.

4. The vaccine vector of claim 1, wherein the CD154 polypeptide has fewer than about 50 amino acids and comprises amino acids 140-149 of SEQ ID NO:26 or a homolog thereof.

5. The vaccine vector of claim 4, wherein the CD154 polypeptide is selected from the group consisting of SEQ ID NO: 6, SEQ ID NO: 7, SEQ ID NO: 27, SEQ ID NO: 28, and SEQ ID NO: 29.

6. The vaccine vector of claim 1, wherein the vaccine vector is a bacterium.

7. The vaccine vector of claim 6, wherein the bacterium is *Salmonella enteritidis*.

8. The vaccine vector of claim 6, wherein the bacterium is a *Salmonella* strain of any of (a) *Salmonella enteritidis* having ATCC deposit number PTA-7871, (b) a *Salmonella* strain capable of colonizing a subject, (c) a *Salmonella* strain comprising a mutation in an aromatization pathway, (d) a *Salmonella* strain comprising a mutation within aroA, (e) a *Salmonella* strain comprising a mutation in a stress response pathway and (f) a *Salmonella* strain comprising a mutation in htrA.

9. A method of enhancing an immune response against the antigenic polypeptide in a subject comprising administering to the subject the vaccine vector of claim 1 in an amount effective to enhance the immune response of the subject to the antigenic polypeptide.

10. The method of claim 9, wherein the subject is selected from the group consisting of human and chicken.

11. The method of claim 9, wherein the antigenic polypeptide is expressed on the surface of the vaccine vector.

12. The method of claim 9, wherein the first polynucleotide and the CD154 polynucleotide are inserted into a third polynucleotide encoding an external portion of a transmembrane protein.

13. The method of claim 9, wherein the CD154 polypeptide has fewer than about 50 amino acids and comprises amino acids 140-149 of SEQ ID NO:26 or a homolog thereof.

14. The method of claim 13, wherein the CD154 polypeptide is selected from the group consisting of SEQ ID NO: 6, SEQ ID NO: 7, SEQ ID NO: 27, SEQ ID NO: 28, and SEQ ID NO: 29.

15. The method of claim 9, wherein the vaccine vector is a bacterium.

16. The method of claim 15, wherein the bacterium is *Salmonella enteritidis*.

17. The method of claim 15, wherein the bacterium is a *Salmonella* strain of any of (a) *Salmonella enteritidis* having ATCC deposit number PTA-7871, (b) a *Salmonella* strain capable of colonizing a subject, (c) a *Salmonella* strain comprising a mutation in an aromatization pathway, (d) a *Salmonella* strain comprising a mutation within aroA, (e) a *Salmonella* strain comprising a mutation in a stress response pathway and (f) a *Salmonella* strain comprising a mutation in htrA.

* * * * *

UNITED STATES PATENT AND TRADEMARK OFFICE
CERTIFICATE OF CORRECTION

PATENT NO. : 10,004,798 B2
APPLICATION NO. : 14/971704
DATED : June 26, 2018
INVENTOR(S) : Walter Bottje et al.

It is certified that error appears in the above-identified patent and that said Letters Patent is hereby corrected as shown below:

On the Title Page

At Item (73) Assignees should read:
The Board of Trustees of the University of Arkansas
The Texas A&M University System Signed and Sealed this
Fourth Day of December, 2018

Andrei Iancu
*Director of the United States Patent and Trademark Office*

SEQUENCE LISTING

```
<160> NUMBER OF SEQ ID NOS: 40

<210> SEQ ID NO 1
<211> LENGTH: 24
<212> TYPE: PRT
<213> ORGANISM: Avian influenza virus

<400> SEQUENCE: 1

Met Ser Leu Leu Thr Glu Val Glu Thr Pro Thr Arg Asn Gly Trp Glu
1               5                   10                  15

Cys Lys Cys Ser Asp Ser Ser Asp
            20

<210> SEQ ID NO 2
<211> LENGTH: 24
<212> TYPE: PRT
<213> ORGANISM: Influenza A virus

<400> SEQUENCE: 2

Met Ser Leu Leu Thr Glu Val Glu Thr Pro Thr Arg Asn Glu Trp Gly
1               5                   10                  15

Cys Arg Cys Asn Asp Ser Ser Asp
            20

<210> SEQ ID NO 3
<211> LENGTH: 24
<212> TYPE: PRT
<213> ORGANISM: Influenza A virus

<400> SEQUENCE: 3

Met Ser Leu Leu Thr Glu Val Glu Thr Pro Ile Arg Asn Glu Trp Gly
1               5                   10                  15

Cys Arg Cys Asn Asp Ser Ser Asp
        20
```

-continued

<210> SEQ ID NO 4
<211> LENGTH: 24
<212> TYPE: PRT
<213> ORGANISM: Influenza A virus

<400> SEQUENCE: 4

Met Ser Leu Leu Thr Glu Val Glu Thr Pro Thr Arg Asn Gly Trp Glu
1               5                   10                  15

Cys Arg Cys Asn Asp Ser Ser Asp
            20

<210> SEQ ID NO 5
<211> LENGTH: 8
<212> TYPE: PRT
<213> ORGANISM: Influenza A virus

<400> SEQUENCE: 5

Glu Val Glu Thr Pro Ile Arg Asn
1               5

<210> SEQ ID NO 6
<211> LENGTH: 11
<212> TYPE: PRT
<213> ORGANISM: Homo sapiens

<400> SEQUENCE: 6

Trp Ala Glu Lys Gly Tyr Tyr Thr Met Ser Cys
1               5                   10

<210> SEQ ID NO 7
<211> LENGTH: 11
<212> TYPE: PRT
<213> ORGANISM: Gallus gallus

<400> SEQUENCE: 7

Trp Met Thr Thr Ser Tyr Ala Pro Thr Ser Ser
1               5                   10

<210> SEQ ID NO 8
<211> LENGTH: 27
<212> TYPE: PRT
<213> ORGANISM: Artificial
<220> FEATURE:
<223> OTHER INFORMATION: Synthetic

<400> SEQUENCE: 8

Gly Gly Gly Trp Ala Glu Lys Gly Tyr Tyr Thr Met Ser Gly Gly Gly
1               5                   10                  15

Glu Val Glu Thr Pro Ile Arg Asn Gly Gly Gly
            20                  25

<210> SEQ ID NO 9
<211> LENGTH: 65
<212> TYPE: PRT
<213> ORGANISM: Artificial
<220> FEATURE:
<223> OTHER INFORMATION: Synthetic

<400> SEQUENCE: 9

Ser Ser Ser Ser Glu Val Glu Thr Pro Thr Arg Asn Ser Ser Ser Glu
1               5                   10                  15

Val Glu Thr Pro Thr Arg Asn Ser Ser Ser Ser Trp Ala Glu Lys Gly
            20                  25                  30

-continued

```
Tyr Tyr Thr Met Ser Ser Ser Ser Glu Val Glu Thr Pro Ile Arg
         35                  40                  45

Asn Ser Ser Ser Ser Glu Val Glu Thr Pro Ile Arg Asn Ser Ser Ser
 50                  55                  60

Ser
 65
```

<210> SEQ ID NO 10
<211> LENGTH: 20
<212> TYPE: DNA
<213> ORGANISM: Salmonella enteritidis

<400> SEQUENCE: 10
tgtacaagtg gacgccaatc                                              20

<210> SEQ ID NO 11
<211> LENGTH: 24
<212> TYPE: DNA
<213> ORGANISM: Salmonella enteritidis

<400> SEQUENCE: 11
gttatcgccg tctttgatat agcc                                         24

<210> SEQ ID NO 12
<211> LENGTH: 20
<212> TYPE: DNA
<213> ORGANISM: Salmonella enteritidis

<400> SEQUENCE: 12
atttcccgtt atgccgcagc                                              20

<210> SEQ ID NO 13
<211> LENGTH: 20
<212> TYPE: DNA
<213> ORGANISM: Salmonella enteritidis

<400> SEQUENCE: 13
gttaaacaga gggcgacgag                                              20

<210> SEQ ID NO 14
<211> LENGTH: 68
<212> TYPE: DNA
<213> ORGANISM: Artificial
<220> FEATURE:
<223> OTHER INFORMATION: Synthetic

<400> SEQUENCE: 14
gctatatcaa agacggcgat aactaactat aacggtccta aggtagcgaa tttccgggga    60
tccgtcga                                                            68

<210> SEQ ID NO 15
<211> LENGTH: 40
<212> TYPE: DNA
<213> ORGANISM: Artificial
<220> FEATURE:
<223> OTHER INFORMATION: Synthetic

<400> SEQUENCE: 15
gctgcggcat aacgggaaat tgtaggctgg agctgcttcg                          40

```
<210> SEQ ID NO 16
<211> LENGTH: 68
<212> TYPE: DNA
<213> ORGANISM: Artificial
<220> FEATURE:
<223> OTHER INFORMATION: Synthetic

<400> SEQUENCE: 16
gctatatcaa agacggcgat aacgaagttg aaaccccgat tcgtaacatt tcccgttatg      60
ccgcagcg                                                              68

<210> SEQ ID NO 17
<211> LENGTH: 73
<212> TYPE: DNA
<213> ORGANISM: Artificial
<220> FEATURE:
<223> OTHER INFORMATION: Synthetic

<400> SEQUENCE: 17
gctatatcaa agacggcgat aactgggcag aaaaaggtta ttataccatg tctatttccc      60
gttatgccgc agc                                                        73

<210> SEQ ID NO 18
<211> LENGTH: 20
<212> TYPE: DNA
<213> ORGANISM: Salmonella enteritidis

<400> SEQUENCE: 18
gccatctcgc ttggtgataa                                                 20

<210> SEQ ID NO 19
<211> LENGTH: 20
<212> TYPE: DNA
<213> ORGANISM: Salmonella enteritidis

<400> SEQUENCE: 19
cgctggtatt ttgcggtaca                                                 20

<210> SEQ ID NO 20
<211> LENGTH: 8
<212> TYPE: PRT
<213> ORGANISM: Influenza A virus

<400> SEQUENCE: 20

Glu Val Glu Thr Pro Thr Arg Asn
1               5

<210> SEQ ID NO 21
<211> LENGTH: 12
<212> TYPE: PRT
<213> ORGANISM: Influenza A virus

<400> SEQUENCE: 21

Leu Leu Ser Arg Ile Asn His Phe Glu Lys Ile Gln
1               5                   10

<210> SEQ ID NO 22
<211> LENGTH: 19
<212> TYPE: PRT
<213> ORGANISM: Influenza A virus
```

<400> SEQUENCE: 22

Ala Asn Pro Ala Asn Asp Leu Cys Tyr Pro Gly Asp Phe Asn Asp Tyr
1               5                   10                  15

Glu Glu Leu

<210> SEQ ID NO 23
<211> LENGTH: 16
<212> TYPE: PRT
<213> ORGANISM: Influenza A virus

<400> SEQUENCE: 23

Gly Arg Leu Ile Gln Asn Ser Ile Thr Ile Glu Arg Met Val Leu Ser
1               5                   10                  15

<210> SEQ ID NO 24
<211> LENGTH: 14
<212> TYPE: PRT
<213> ORGANISM: Influenza A virus

<400> SEQUENCE: 24

Thr Tyr Gln Arg Thr Arg Ala Leu Val Arg Thr Gly Met Asp
1               5                   10

<210> SEQ ID NO 25
<211> LENGTH: 272
<212> TYPE: PRT
<213> ORGANISM: Gallus gallus

<400> SEQUENCE: 25

Met Asn Glu Ala Tyr Ser Pro Ala Ala Pro Arg Pro Met Gly Ser Thr
1               5                   10                  15

Ser Pro Ser Thr Met Lys Met Phe Met Cys Phe Leu Ser Val Phe Met
                20                  25                  30

Val Val Gln Thr Ile Gly Thr Val Leu Phe Cys Leu Tyr Leu His Met
            35                  40                  45

Lys Met Asp Lys Met Glu Glu Val Leu Ser Leu Asn Glu Asp Tyr Ile
    50                  55                  60

Phe Leu Arg Lys Val Gln Lys Cys Gln Thr Gly Glu Asp Gln Lys Ser
65                  70                  75                  80

Thr Leu Leu Asp Cys Glu Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
        115                 120                 125

Ala Glu Glu Lys Arg Gln Pro Ile Ala Thr His Leu Ala Gly Val Lys
    130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
        195                 200                 205

```
Met Glu Glu Asp Arg Leu Leu Met Lys Gly Leu Asp Thr His Ser Thr
210                 215                 220
Ser Thr Ala Leu Cys Glu Leu Gln Ser Ile Arg Glu Gly Gly Val Phe
225                 230                 235                 240
Glu Leu Arg Gln Gly Asp Met Val Phe Val Asn Val Thr Asp Ser Thr
            245                 250                 255
Ala Val Asn Val Asn Pro Gly Asn Thr Tyr Phe Gly Met Phe Lys Leu
            260                 265                 270
```

<210> SEQ ID NO 26
<211> LENGTH: 261
<212> TYPE: PRT
<213> ORGANISM: Homo sapiens

<400> SEQUENCE: 26

```
Met Ile Glu Thr Tyr Asn Gln Thr Ser Pro Arg Ser Ala Ala Thr Gly
1               5                   10                  15
Leu Pro Ile Ser Met Lys Ile Phe Met Tyr Leu Leu Thr Val Phe Leu
                20                  25                  30
Ile Thr Gln Met Ile Gly Ser Ala Leu Phe Ala Val Tyr Leu His Arg
            35                  40                  45
Arg Leu Asp Lys Ile Glu Asp Glu Arg Asn Leu His Glu Asp Phe Val
50                  55                  60
Phe Met Lys Thr Ile Gln Arg Cys Asn Thr Gly Glu Arg Ser Leu Ser
65                  70                  75                  80
Leu Leu Asn Cys Glu Glu Ile Lys Ser Gln Phe Glu Gly Phe Val Lys
                85                  90                  95
Asp Ile Met Leu Asn Lys Glu Glu Thr Lys Lys Glu Asn Ser Phe Glu
            100                 105                 110
Met Gln Lys Gly Asp Gln Asn Pro Gln Ile Ala Ala His Val Ile Ser
        115                 120                 125
Glu Ala Ser Ser Lys Thr Thr Ser Val Leu Gln Trp Ala Glu Lys Gly
130                 135                 140
Tyr Tyr Thr Met Ser Asn Asn Leu Val Thr Leu Glu Asn Gly Lys Gln
145                 150                 155                 160
Leu Thr Val Lys Arg Gln Gly Leu Tyr Tyr Ile Tyr Ala Gln Val Thr
                165                 170                 175
Phe Cys Ser Asn Arg Glu Ala Ser Ser Gln Ala Pro Phe Ile Ala Ser
            180                 185                 190
Leu Cys Leu Lys Ser Pro Gly Arg Phe Glu Arg Ile Leu Leu Arg Ala
        195                 200                 205
Ala Asn Thr His Ser Ser Ala Lys Pro Cys Gly Gln Gln Ser Ile His
210                 215                 220
Leu Gly Gly Val Phe Glu Leu Gln Pro Gly Ala Ser Val Phe Val Asn
225                 230                 235                 240
Val Thr Asp Pro Ser Gln Val Ser His Gly Thr Gly Phe Thr Ser Phe
                245                 250                 255
Gly Leu Leu Lys Leu
            260
```

<210> SEQ ID NO 27
<211> LENGTH: 10
<212> TYPE: PRT
<213> ORGANISM: Anas sp.

<400> SEQUENCE: 27

Trp Asn Lys Thr Ser Tyr Ala Pro Met Asn
1               5                   10

<210> SEQ ID NO 28
<211> LENGTH: 10
<212> TYPE: PRT
<213> ORGANISM: Mus sp.

<400> SEQUENCE: 28

Trp Ala Lys Lys Gly Tyr Tyr Thr Met Lys
1               5                   10

<210> SEQ ID NO 29
<211> LENGTH: 10
<212> TYPE: PRT
<213> ORGANISM: Bos taurus

<400> SEQUENCE: 29

Trp Ala Pro Lys Gly Tyr Tyr Thr Leu Ser
1               5                   10

<210> SEQ ID NO 30
<211> LENGTH: 18
<212> TYPE: DNA
<213> ORGANISM: Artificial
<220> FEATURE:
<223> OTHER INFORMATION: Synthetic

<400> SEQUENCE: 30
tagggataac agggtaat                                                   18

<210> SEQ ID NO 31
<211> LENGTH: 20
<212> TYPE: DNA
<213> ORGANISM: Artificial
<220> FEATURE:
<223> OTHER INFORMATION: Synthetic

<400> SEQUENCE: 31
caaaagcgct ctgaagttcc                                                 20

<210> SEQ ID NO 32
<211> LENGTH: 20
<212> TYPE: DNA
<213> ORGANISM: Artificial
<220> FEATURE:
<223> OTHER INFORMATION: Synthetic

<400> SEQUENCE: 32
gcgtgagggg atcttgaagt                                                 20

<210> SEQ ID NO 33
<211> LENGTH: 92
<212> TYPE: DNA
<213> ORGANISM: Artificial
<220> FEATURE:
<223> OTHER INFORMATION: Synthetic

<400> SEQUENCE: 33
tgggcagaaa aaggttatta taccatgtct ggtggtggtg aagttgaaac cccgattcgt     60
aacggtggtg gtatttcccg ttatgccgca gc                                   92

<210> SEQ ID NO 34
<211> LENGTH: 63
<212> TYPE: DNA
<213> ORGANISM: Artificial
<220> FEATURE:
<223> OTHER INFORMATION: Synthetic

<400> SEQUENCE: 34
agacatggta taataacctt tttctgccca accaccaccg ttatcgccgt ctttgatata     60
gcc                                                                  63

<210> SEQ ID NO 35
<211> LENGTH: 134
<212> TYPE: DNA
<213> ORGANISM: Artificial
<220> FEATURE:
<223> OTHER INFORMATION: Synthetic

<400> SEQUENCE: 35
tgggcagaaa aaggttatta taccatgtct tcctcctcct ccgaagttga aaccccgatt     60
cgtaactcct cctcctccga agttgaaacc ccgattcgta actcctcctc ctccatttcc    120
cgttatgccg cagc                                                     134

<210> SEQ ID NO 36
<211> LENGTH: 138
<212> TYPE: DNA
<213> ORGANISM: Artificial
<220> FEATURE:
<223> OTHER INFORMATION: Synthetic

<400> SEQUENCE: 36
agacatggta taataacctt tttctgccca ggaggaggag gagttacggg tcggggtttc     60
aacttcggag gaggaggagt tacgggtcgg ggtttcaact tcggaggagg aggagttatc    120
gccgtctttg atatagcc                                                 138

<210> SEQ ID NO 37
<211> LENGTH: 24
<212> TYPE: DNA
<213> ORGANISM: Influenza A virus

<400> SEQUENCE: 37
gaagttgaaa ccccgattcg taac                                           24

<210> SEQ ID NO 38
<211> LENGTH: 30
<212> TYPE: DNA
<213> ORGANISM: Artificial
<220> FEATURE:
<223> OTHER INFORMATION: Synthetic

<400> SEQUENCE: 38
tgggcagaaa aaggttatta taccatgtct                                     30

<210> SEQ ID NO 39
<211> LENGTH: 81
<212> TYPE: DNA
<213> ORGANISM: Artificial
<220> FEATURE:
<223> OTHER INFORMATION: Synthetic

```
<400> SEQUENCE: 39
ggtggtggtt gggcagaaaa aggttattat accatgtctg gtggtggtga agttgaaacc    60
ccgattcgta acggtggtgg t                                              81

<210> SEQ ID NO 40
<211> LENGTH: 198
<212> TYPE: DNA
<213> ORGANISM: Artificial
<220> FEATURE:
<223> OTHER INFORMATION: Synthetic

<400> SEQUENCE: 40
tcctcctcct ccgaagttga aacccgacc cgtaactcct cctcctccga agttgaaacc    60
ccgacccgta actcctcctc ctcctgggca gaaaaaggtt attataccat gtcttcctcc   120
tcctccgaag ttgaaacccc gattcgtaac tcctcctcct ccgaagttga aacccgatt    180 cgtaactcct cctcctcc                                                 198
```